(12) United States Patent
Taylor et al.

(10) Patent No.: US 12,208,212 B2
(45) Date of Patent: *Jan. 28, 2025

(54) GAS CONCENTRATOR WITH REMOVABLE CARTRIDGE ADSORBENT BEDS

(71) Applicant: Inogen, Inc., Goleta, CA (US)

(72) Inventors: Brenton Taylor, Kenwood, CA (US); Peter Hansen, Santa Barbara, CA (US); Patrick Burgess, Dunedin, FL (US); Daniel Chin, Goleta, CA (US)

(73) Assignee: Inogen, Inc., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/977,597

(22) Filed: Oct. 31, 2022

(65) Prior Publication Data

US 2023/0120744 A1 Apr. 20, 2023

Related U.S. Application Data

(63) Continuation of application No. 16/915,847, filed on Jun. 29, 2020, now Pat. No. 11,484,680, which is a continuation of application No. 15/608,788, filed on May 30, 2017, now Pat. No. 10,695,520, which is a continuation-in-part of application No. 15/427,948, (Continued)

(51) Int. Cl.
| | |
|---|---|
| *A61M 16/10* | (2006.01) |
| *A61M 16/06* | (2006.01) |
| *B01D 53/04* | (2006.01) |
| *C01B 13/02* | (2006.01) |
| *B01D 53/047* | (2006.01) |

(52) U.S. Cl.
CPC ........ *A61M 16/10* (2013.01); *A61M 16/0677* (2014.02); *A61M 16/101* (2014.02); *B01D 53/0415* (2013.01); *C01B 13/0259* (2013.01); *A61M 16/107* (2014.02); *A61M 2202/0208* (2013.01); *A61M 2205/8206* (2013.01); *A61M 2209/088* (2013.01); *B01D 53/047* (2013.01); *B01D 2253/108* (2013.01); *B01D 2256/12* (2013.01); *B01D 2257/102* (2013.01); *B01D 2257/504* (2013.01); *B01D 2257/80* (2013.01); *B01D 2259/4533* (2013.01); *B01D 2259/4541* (2013.01); *Y02C 20/40* (2020.08); *Y02P 20/151* (2015.11)

(58) Field of Classification Search
CPC .............. A61M 16/10; A61M 16/0677; A61M 16/101; A61M 2202/0208; A61M 2205/8206; A61M 2209/088; B01D 2256/12

See application file for complete search history.

(56) References Cited

U.S. PATENT DOCUMENTS

| | | |
|---|---|---|
| 4,094,775 A | 6/1978 | Mueller |
| 4,378,982 A | 4/1983 | McCombs |

(Continued)

*Primary Examiner* — Timothy A Stanis
(74) *Attorney, Agent, or Firm* — Knobbe, Martens, Olson & Bear, LLP

(57) ABSTRACT

A portable oxygen concentrator designed for medical use where the sieve beds, adsorbers, are designed to be replaced by a patient. The concentrator is designed so that the beds are at least partially exposed to the outside of the system and can be easily released by a simple user-friendly mechanism. Replacement beds may be installed easily by patients, and all gas seals will function properly after installation.

20 Claims, 27 Drawing Sheets

Related U.S. Application Data filed on Feb. 8, 2017, now Pat. No. 10,786,644, which is a continuation of application No. 13/066,716, filed on Apr. 22, 2011, now Pat. No. 9,592,360.

(56) References Cited

U.S. PATENT DOCUMENTS

| | | | |
|---|---|---|---|
| 4,530,706 A | 7/1985 | Jones | |
| 4,826,510 A | 5/1989 | McCombs | |
| 4,865,231 A | 9/1989 | Wiercinski | |
| 4,971,609 A | 11/1990 | Pawlos | |
| 5,275,642 A | 1/1994 | Bassine | |
| 5,578,115 A | 11/1996 | Cole | |
| 5,863,425 A | 1/1999 | Herlehy | |
| 5,989,314 A | 11/1999 | Schaub et al. | |
| 6,092,811 A | 7/2000 | Bojarczuk | |
| 6,149,138 A | 11/2000 | Birdsell | |
| 6,190,441 B1 | 2/2001 | Czabala | |
| 6,520,176 B1 | 2/2003 | Dubois | |
| 6,651,658 B1 | 11/2003 | Hill | |
| 6,691,702 B2 | 2/2004 | Appel | |
| 6,755,895 B2 | 6/2004 | Lomax | |
| 7,000,894 B2 | 2/2006 | Olson | |
| 7,135,059 B2 * | 11/2006 | Deane | B01D 53/0415 96/135 |
| 7,490,865 B1 | 2/2009 | Tsai | |
| 7,604,005 B2 | 10/2009 | Jagger | |
| 8,894,751 B2 | 11/2014 | Galbraith | |
| 9,199,055 B2 | 12/2015 | Galbraith | |
| 2003/0005928 A1 | 1/2003 | Appel et al. | |
| 2005/0045041 A1 | 3/2005 | Hechinger | |
| 2005/0072426 A1 | 4/2005 | Deane | |
| 2005/0103341 A1 | 5/2005 | Deane | |
| 2006/0117957 A1 | 6/2006 | McCombs | |
| 2006/0174874 A1 | 8/2006 | Jagger | |
| 2006/0174882 A1 | 8/2006 | Jagger | |
| 2006/0230929 A1 * | 10/2006 | Bliss | B01D 53/0407 95/96 |
| 2007/0056584 A1 | 3/2007 | Jagger | |
| 2007/0137487 A1 | 6/2007 | Whitley | |
| 2010/0052293 A1 | 3/2010 | Brooks | |
| 2012/0055340 A1 | 3/2012 | Wilkinson | |
| 2012/0167888 A1 | 7/2012 | Taylor | |
| 2012/0192864 A1 | 8/2012 | Galbraith | |
| 2012/0291884 A1 | 11/2012 | Yamaura et al. | |
| 2012/0304867 A1 | 12/2012 | Watanabe et al. | |
| 2013/0008438 A1 | 1/2013 | Sugawara et al. | |
| 2013/0299005 A1 | 11/2013 | Enomoto et al. | |

\* cited by examiner

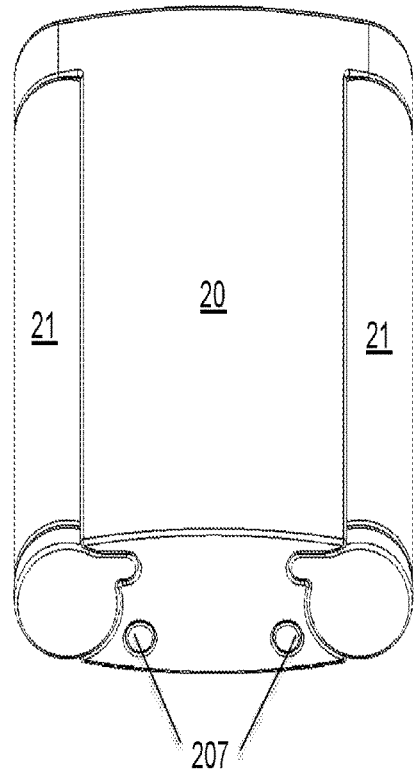
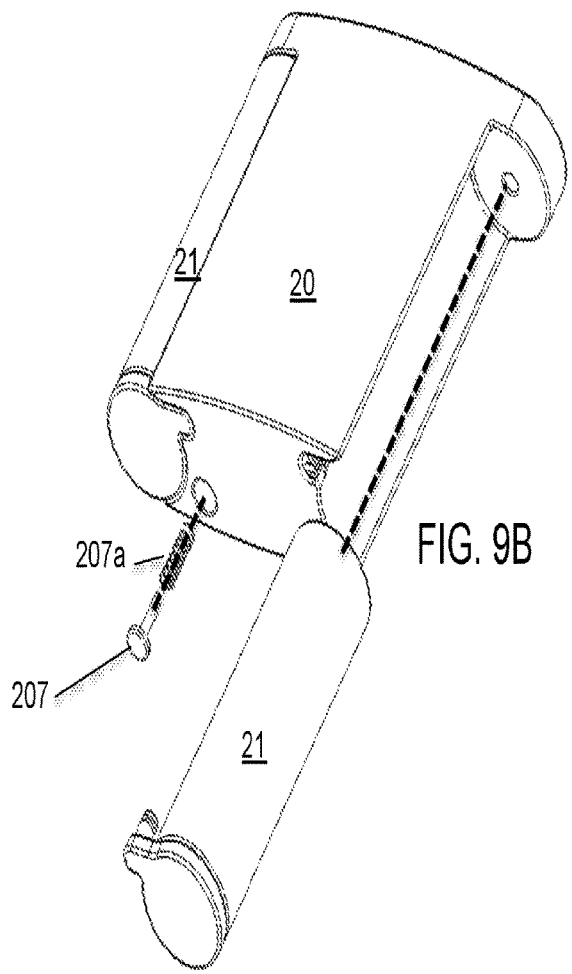
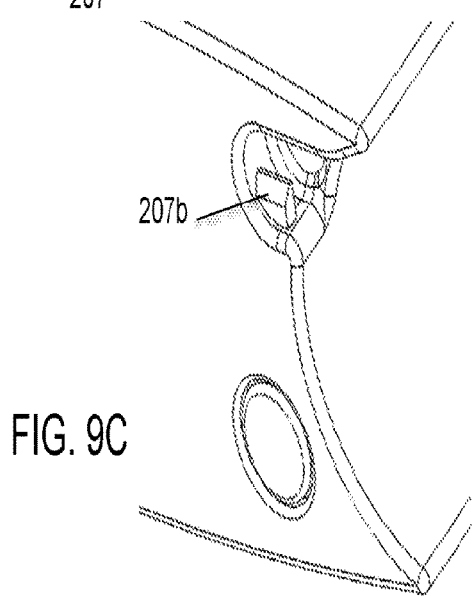
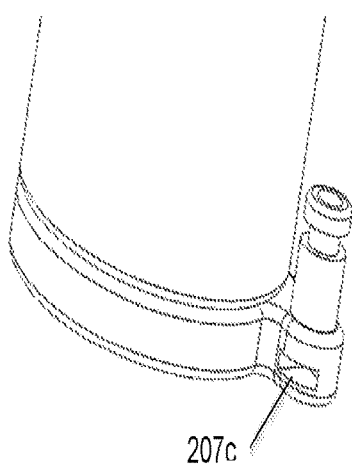
FIG. 9A
FIG. 9B
FIG. 9C
FIG. 9D

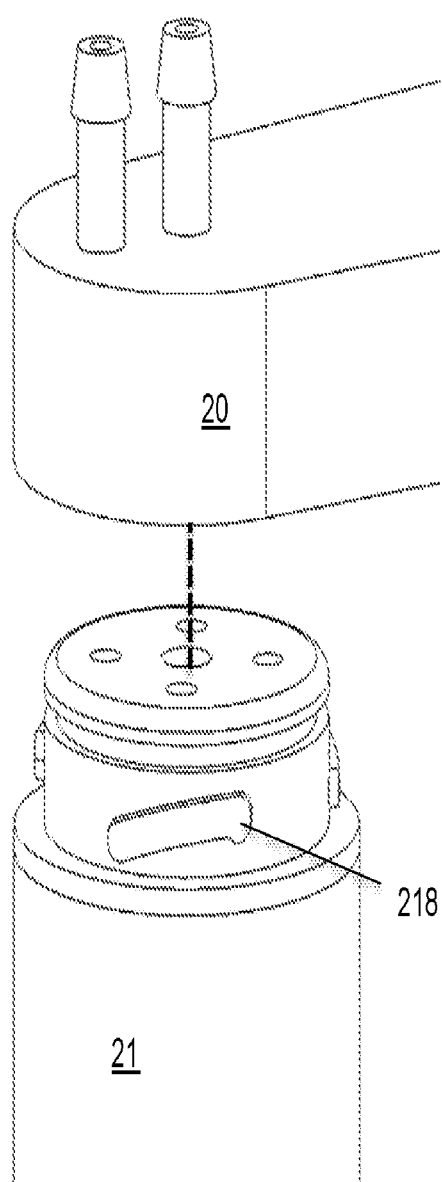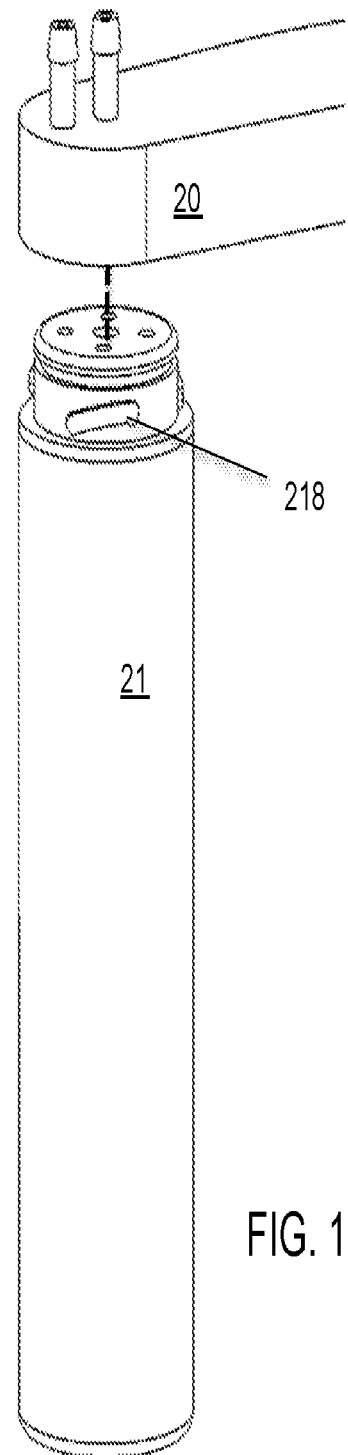
FIG. 13A
FIG. 13B

GAS CONCENTRATOR WITH REMOVABLE CARTRIDGE ADSORBENT BEDS

RELATED APPLICATIONS

This Application is a Continuation of U.S. application Ser. No. 16/915,847, filed Jun. 29, 2020, which is a Continuation of U.S. application Ser. No. 15/608,788 filed May 30, 2017 which is a Continuation-in-Part of U.S. application Ser. No. 15/427,948, filed Feb. 8, 2017 which in turn is a Continuation of U.S. application Ser. No. 13/066,716, filed Apr. 22, 2011

FEDERALLY SPONSORED RESEARCH

Not Applicable

SEQUENCE LISTING

Not Applicable

BACKGROUND OF THE INVENTION

The invention generally relates to gas concentrators, and more particularly relates to medical oxygen concentrators used by patients in the home care setting where cost and frequency of maintenance performed by a technician should be minimized.

The application of oxygen concentrators for therapeutic use is known, and many variants of such devices exist. A particularly useful class of oxygen concentrators is designed to be portable, allowing users to move about and to travel for extended periods of time without the need to carry a supply of stored oxygen or to have any maintenance performed on their equipment. These portable oxygen concentrators are typically in the range of 2 to 20 lbs and produce from 0.3 to 5.0 LPM of oxygen. Most of these portable concentrators are based on Pressure Swing Adsorption (PSA), Vacuum Pressure Swing Adsorption (VPSA), or Vacuum Swing Adsorption (VSA) designs which feed compressed air to selective adsorption beds. In a typical oxygen concentrator, the beds utilize a zeolite adsorbent to selectively adsorb nitrogen, resulting in pressurized, oxygen-rich product gas.

The main elements in a typical portable therapeutic oxygen concentrator are shown in FIG. 1. Air is drawn in, and typically filtered, at air inlet 1 before being pressurized by compressor 2 to a pressure of 1.2 to 2.5 atmospheres. The pressurized air is directed by a valve arrangement through adsorbent beds 3. An exemplary adsorbent bed implementation, used in a concentrator design developed by the inventors, is two columns filled with a lithium exchanged zeolite adsorbent in the ratio of about 1 gram of adsorbent per 1-10 ml of oxygen produced per minute. The pressurized air is directed through these adsorber vessels or columns in a series of steps which constitute a gas separation cycle, often a PSA cycle or some variation including vacuum instead of, or in conjunction with, compression yielding overall compression ratios of about 1.5:1 to 4.0:1. Although many different arrangements of adsorber vessels and gas separation cycles are possible, the result is that nitrogen is removed by the adsorbent material, and the resulting oxygen rich gas is routed to a product gas storage device at 4. Some of the oxygen product gas can be routed back through the bed to flush out (purge) the adsorbed nitrogen to an exhaust 6. Generally multiple adsorbent beds, or columns in the exemplary device, are used so at least one bed may be used to make product while at least one other bed is being purged, ensuring a continuous flow of product gas. The purged gas is exhausted from the concentrator at the exhaust 6.

Such gas separation systems are known in the art, and it is appreciated that the gas flow control through the compressor and the adsorbent beds is complex and requires precise timing and control of parameters such as pressure, flow rate, and temperature to attain the desired oxygen concentration of 80% to 95% purity in the product gas stream. Accordingly, most modern concentrators also have a programmable controller 5, typically a microprocessor, to monitor and control the various operating parameters of the gas separation cycle. In particular, the controller controls the timing and operation of the various valves used to cycle the beds through feed, purge, and pressure equalization steps which make up the gas separation cycle. Also present in most portable concentrators is a conserver 7 which acts to ensure that oxygen rich gas is only delivered to a patient during inhalation. Thus, less product gas is delivered than by means of a continuous flow arrangement, thereby allowing for smaller, lighter concentrator designs. A pulse of oxygen rich air, called a bolus, is delivered in response to a detected breath via the conserver. Using a conserver in conjunction with a gas concentrator may reduce the amount of oxygen required to maintain patient oxygen saturation by a factor of about 2:1 to 9:1. A typical concentrator will also contain a user/data interface 8 including elements such as an LCD display, alarm LEDs, audible buzzers, wireless data interface devices, data ports, and control buttons. In addition to the above subsystems, most portable oxygen concentrators contain at least one rechargeable battery and a charging system to power the concentrator while away from an AC or DC power source. These battery systems are typically composed of lithium ion cells The battery systems can power the concentrator from 2-12 hours depending on the amount of oxygen required by the patient, device efficiency, and the capacity of the battery pack which may range from about 40 Watt-hours to 250 Watt-hours on systems with multiple battery packs. Additionally the concentrator charging system may boost battery or input voltages to efficiently run system components or charge batteries from a lower voltage power source like a automotive DC power source.

To be practical and usable by an individual needing therapeutic oxygen, portable oxygen concentrators should be less than about 2100 cubic inches and preferably less than 600 cubic inches in total volume, less than about 20 pounds and preferably less than 5 pounds in weight, and produce less than about 45 decibels of audible noise, while retaining the capacity to produce a flow of product gas adequate to provide for a patient's oxygen needs, usually a flow rate prescribed by a medical practitioner in about the range of 1 LPM to 6 LPM or more particularly, to maintain a blood oxygen saturation level of 90% or greater. Further, a portable medical oxygen concentrator must work under varied environmental conditions such as 0° C. to 40° C. and 0%-95% relative humidity without costly or frequent service or maintenance requirements. Although fixed site PSA based concentrators have been available for many years, such fixed site units may weigh 30-50 pounds or more, be several cubic feet in volume, and produce sound levels greater than 45 dBA. Thus portable concentrators involve a significant amount of miniaturization, leading to smaller, more complex designs compared to stationary units. System size, weight, and complexity may lead to fewer mitigative options or design choices against contamination and other wear and tear effects that can lead to an unacceptably short maintenance interval when the portable concentrators may be required to supply oxygen around the clock.

One particular challenge of portable concentrator design is that the adsorbent beds must by necessity be small, yet capable of producing an adequate quantity of product gas. A portable oxygen concentrator might require oxygen production of greater than 3 ml of oxygen per minute per gram of adsorbent in order to achieve an acceptable size of less than 600 cubic inches. Since the adsorbent beds are optimized for $O_2$ production per gram of adsorbent, any significant decrease in capacity of the beds over time can result in decreased product purity as the required $O_2$ production per gram of active adsorbent exceeds the limits of the adsorbent and PSA cycle operating parameters. One contributing factor that can lead to a decrease in bed capacity is the adsorption of impurities that do not completely desorb during normal process operation, leading to the accumulation and retention of impurities in the beds and therefore less active adsorbent than originally intended in the design. An example of such an impurity that reduces the adsorption capacity of many zeolites used in air separation is water. Some stationary concentrators utilize some means of removing water from the compressed gas before feeding the adsorbent beds, but most rely on an excess quantity of adsorbent to allow for contamination over time. Portable concentrators, by the nature of their application, are more likely to be exposed to a wide range of operating conditions including high humidity environments and/or rapid temperature changes that could result in the need for more frequent zeolite replacement. If water is present, either in the form of liquid (condensed out of the compressed air feedstream) or vapor, and enters the molecular sieve beds, the beds will irreversibly adsorb at least some of this water during each adsorption cycle. The energy of adsorption of water on lithium exchanged zeolites used in air separation is very high and not all water adsorbed during the adsorption steps in the process is desorbed during evacuation/purge of the beds under typical PSA cycle operating parameters. Therefore, complete removal of adsorbed water from zeolite beds usually entails applying some sort of energy to the beds, such as thermal, infrared, or microwave, and purging with a dry gas or applying a vacuum to the beds during the regeneration process. These regeneration processes are impractical in a portable concentrator due to high temperature or high power requirements. As a result, the accumulation of adsorbed water over time results in a reduction in capacity of the beds, as fewer sites are available for nitrogen binding. Fewer binding sites in the adsorbent bed can result in a decrease in product purity over time as nitrogen passes through the sieve beds and dilutes the oxygen product gas, and shortens the service life or service interval of the concentrator. Many zeolites used in air separation, and in particular advanced adsorbents, particularly the high lithium containing low silica X type zeolite (LiLSX) used in portable concentrators, are hydrophilic in their activated state due to the interaction of the strong dipole moment of water molecules with the electric fields present in the LiLSX cages and can therefore be prone to this problem. In the effort to make more compact and efficient concentrators, PSA cycle frequencies can increase to rates approaching 10 cycles per minute and adsorbent productivity increases accordingly with advances in process and adsorbent technology to productivities exceeding 10.0 ml of oxygen per minute per gram of adsorbent. The corresponding decrease in adsorbent inventory exacerbates the problem as the amount of gas processed per unit of adsorbent increases proportionally, (the bed size factor decreases) and the presence of impurities in the process gas can deactivate the adsorbents at a much faster rate than with conventional PSA processes, as described in U.S. Pat. Nos. 7,037,358 and 7,160,367, which are incorporated by reference herein.

It is therefore necessary to design portable oxygen concentrators such that zeolite contamination can be prevented or handled in a manner that avoids costly or frequent maintenance by a field technician or equipment provider. While the inventors have previously disclosed a system that achieves long sieve bed life by removing water prior to the feed gas contacting the zeolite in U.S. Pat. Nos. 7,780,768 and 8,580,015, whose teachings are incorporated by reference, this approach adds size and cost to the system to achieve its resistance to zeolite contamination. It is therefore desirable to design a portable oxygen concentrator that minimizes size and weight as a function of oxygen output with commonly available commercial adsorbents such as Z12-49 or OP-76 manufactured by Zeochem, Nitroxy SXSDM, Nitroxy Revolution or Nitroxy NeXT manufactured by Arkema, or Oxysiv MDX manufactured by UOP. While eliminating water removal components such as membrane air dryers or pretreatment layers such as activated alumina or an NaX type zeolite will reduce the size and weight of the sieve beds it will also reduce the service life of the sieve beds to an unacceptable level. Oxygen equipment used for Long Term Oxygen Therapy (LTOT) is optimally deployed for 3-5 years without any service requirements. Any service requirement within that time interval simply adds to the overall cost of the equipment, which substantially reverses any cost benefit gained by removing a membrane air dryer or pretreatment layer. Further, allowing sieve bed contamination without prevention or service may lead to providing 82-87% purity oxygen instead of 87-95% pure oxygen to the patient. At this time, portable oxygen concentrator adoption will require smaller, lighter devices that do not require field service by a technician or equipment provider, but also minimize size and cost of the equipment.

A typical adsorbent bed or adsorber is constructed of a column with an inlet port and an outlet port arranged at opposite ends. The inlet port is used for admitting pressurized feed gas from the compressor as well as exhausting the waste gas out of the system in the countercurrent (opposite to the direction of flow of the feed gas) direction. The outlet port allows product gas to flow to the accumulator or output where it can be delivered to the patient. The outlet port also admits product gas back into the exhausted sieve bed in the countercurrent direction to purge the column of remaining waste gas prior to introducing additional feed gas. Inlet and outlet ports must create a sealed connection to allow pressurized feed gas and product gas to pass into and out of the columns without wasteful leaks that would upset the balance of the system or let oxygen rich product gas escape from the system. The inlet and outlet port connections are typically composed of barb fittings, quick connect fittings, tapered pipe thread fittings, or integrated manifold connections such as adhesives, face seals, gaskets, o-rings or straight threads. The adsorbers would typically be connected to the valve manifold of the concentrator through tubing or a direct manifold connection. Either prior art construction method resulted in a robust pneumatic connection that was only meant to be disconnected by a trained service technician who could access the internal components of the concentrator and disconnect or disassemble the inlet and outlet connections. Some columns, such as those that are adhesive bonded to an integrated manifold, may not be removable at all in a field service environment and must be replaced in combination with other system components to achieve zeolite replacement.

BRIEF SUMMARY OF THE INVENTION

The invention is a portable oxygen concentrator platform, including a PSA/VPSA/VSA core section capable of mating with user replaceable adsorbers. The core section includes all of the concentrator instrumentation, mechanics, and pneumatics other than the adsorbers and includes a housing; a controller; a user interface; at least one compressor, air control valve, and air filter, comprising a PSA/VPSA/VSA oxygen system when mated with user replaceable adsorbers; and a patient delivery apparatus. The core also includes at least one adsorber receptacle that is capable of mating to a user replaceable adsorber. The receptacle includes at least two pressure sealed gas connections to inlet and outlet ports of the core section, at least two easily disconnectable pressure sealed gas connectors for mating to an inlet and outlet port on a user replaceable adsorber, and a user operable adsorber retention mechanism. Mating a user replaceable adsorber with the adsorber receptacle forms a complete portable oxygen concentrator. The invention is applicable to the portable medical concentrator field where the concentrator preferably weighs less than 10 pounds, produces less than 45 dba acoustic noise when operating, and has an output gas flow of 5 lpm or less and has rechargeable battery capable of running the concentrator for greater than 2 hours. In a preferred embodiment, the concentrator weighs less than about 5 pounds.

The invention also may be a combination of the platform section and at least one user replaceable adsorber, forming a complete portable concentrator. The user replaceable adsorber capable of mating with compatible portable oxygen concentrator platform includes at least one selective adsorbent, disconnectable pressure sealed gas connectors for mating to the platform receptacle inlet and outlet connectors, and mating retention mechanism to the platform adsorber receptacle retention mechanism.

In certain embodiments, the battery mounts to the instrumentation section and prevents removal of the adsorbers while the battery is attached, and there may be a removable case that encloses the platform, user replaceable adsorber beds and battery when all three are mounted together.

In other embodiments the inlet and outlet ports may include one or more radial seals, and the adsorber and receptacle ports insert beyond the radial seal by at least 1-5 mm. The leak rate of the seals is preferably less than about 10 SCCM over the device operating pressure or vacuum level of the adsorber which may be from 0.2 atmospheres to 3.0 atmospheres. In certain embodiments the adsorber ports are coaxial with the receptacle ports. In other embodiments pneumatic gas seals may include one or more face seals where portions of the adsorbent bed structures are common to more than one adsorber.

In some embodiments either the platform or adsorber retention mechanism comprises a sliding spring loaded plunger and the corresponding mating retention mechanism includes a slot which mates with the plunger. The spring loaded plunger snaps into the slot when the adsorber is mated to the platform thereby retaining the adsorber and actuation of the plunger releases the adsorber. The retention force of the release mechanism is preferably less than about three pounds, and the plunger may be finger actuated to release the adsorber.

In other embodiments, either the platform or adsorber retention mechanism includes a screw operated tab and the corresponding mating retention mechanism includes a slot which mates with the tab. The tab is rotated into the slot when the adsorber is mated to the platform thereby retaining the adsorber and reverse rotation of the tab releases the adsorber.

In other embodiments, the platform retention mechanism includes a push button actuated spring loaded plunger and the adsorber retention mating hardware includes a slot which mates with the plunger. The spring loaded plunger snaps into the slot when the adsorber is mated to the platform thereby retaining the adsorber and push button actuation of the plunger releases the adsorber. The adsorber is preferably released with less than about 25 Newtons of force applied to the push button, and the removable adsorber mates to the instrument section in an axis perpendicular to the flow of gas through the column.

In some embodiments, the adsorber receptacle gas connections are connected to the air control valves by compliant pressure members. In a particular version, the adsorber receptacle gas connectors are directly connected to the compliant members, and when connected to the compliant members, are held in place by a housing mounting element structurally independent from the receptacle gas connector. In an alternative embodiment at least one of the gas connections could be directly to a manifold.

In other embodiments, the platform retention mechanism includes a threaded adsorber and threaded adsorber receptacle. The inlet and outlet ports may be coaxial and located on one end of the adsorber. The adsorber or the adsorber receptacle have radial seals that enable the sealing of the gas connection in any rotational orientation around the center axis of the adsorber.

In certain embodiments, the adsorber is retained to the receptacle by a twist to lock mechanism. The twist lock may be engaged by less than about 180 degrees of rotation, and the inlet and outlet ports may be coaxial and located on one end of the adsorber.

In other embodiments, the platform retention mechanism includes a hinged cover. The hinged cover snaps into place when the adsorber is mated to the platform thereby retaining the adsorber, and opening the cover releases the adsorber. The hinged cover may preferably be disengaged with less than about 25 Newtons of force and can be operated by a finger.

In other embodiments, one of the inlet or outlet ports is rigidly mounted to the receptacle by any of a twist to lock or threaded engagement and at least one of the inlet of outlet port connections is made by attaching a flexible tube to the port.

In one or more embodiments, a portable oxygen concentrator, may be provided including a platform, including a housing, a controller, a user interface, at least one compressor, air control valve, and air filter, an oxygen delivery apparatus, at least one adsorber receptacle including at least one gas connector port and at least one adsorber retention element; and at least two separable user replaceable adsorbers including an adsorber having a top end and a bottom end, the adsorber configured to contain a nitrogen selective adsorbent material, wherein a flow axis of gas through the column may be between the top and bottom ends, at least one retention element on the adsorber configured to mate directly with an adsorber receptacle retention element and, a first and a second disconnectable pressure sealed gas connector disposed on the top and bottom ends of the column respectively, wherein the gas connectors may be in fluid communication with the adsorbent and may extend at least one of in parallel or perpendicularly to the flow axis in substantially the same direction and the central axes of the gas connectors may be substantially parallel to each other;

wherein the adsorbers may be configured to mate with the platform to form a complete oxygen concentrator, the retention mechanism may be accessible on the exterior of the platform, and at least one of the adsorber or the adsorber receptacle retention mechanisms may be hand operable; and at least two adsorbers may be attached together and have a common retention mechanism; wherein the concentrator weighs less than 10 pounds, produces less than 45 decibels acoustic noise when operating, and has an output gas flow of 5 liters per minute or less and has a rechargeable battery capable of running the concentrator for greater than 2 hours.

In some embodiments, the common member may be disposed at one end of the two adsorbers and may include at least one of the input or output ports. In other embodiments an additional common member may be disposed at the other end of the two adsorbers. In some embodiments the additional common member may contain at least one of the input or output ports. In other embodiments the common member may form a portion of the adsorber seal. In other embodiments the adsorber may contain a flared edge that forms an additional portion of the adsorber seal. In some embodiments the seal may be clamped in place by an additional common member. In other embodiments the seal may be a face seal between the common member and the adsorber column. In some embodiments the adsorbers may be configured with dimensions to at least one of minimize the width of the two attached adsorbers or minimize the length of the two attached adsorbers. In some embodiments the adsorbers when mated are accessible from the exterior of the platform.

BRIEF DESCRIPTION OF THE DRAWINGS

The understanding of the following detailed description of certain preferred embodiments of the invention will be facilitated by referring to the accompanying figures.

FIGS. 9A, 9B, 9C, and 9D depict another example of a suitable user actuatable adsorber retention mechanism.

FIGS. 13A and 13B depict a twist-lock adsorber interface.

DETAILED DESCRIPTION OF THE INVENTION

Figure 1:
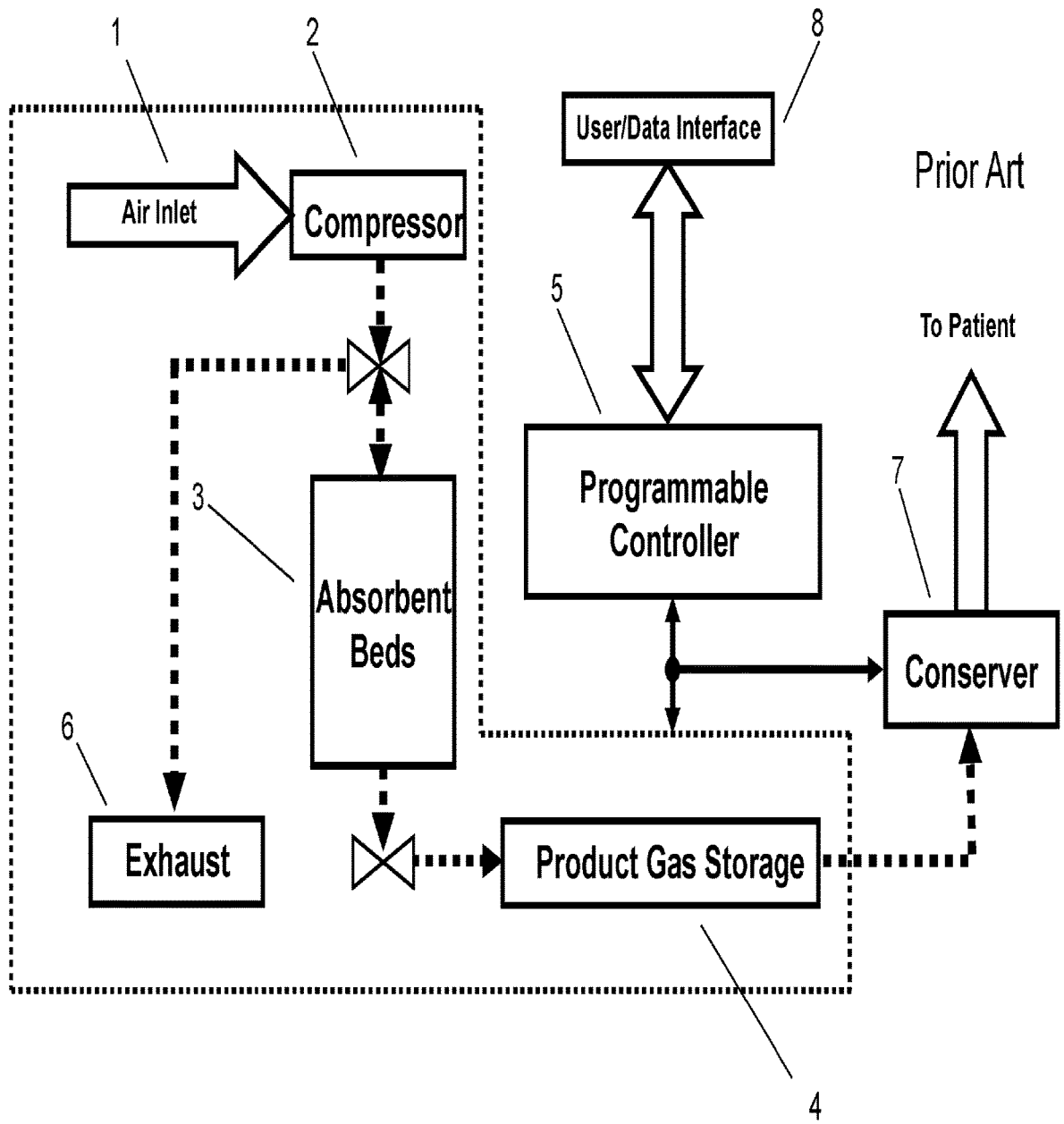
FIG. 1 shows the general elements of gas concentrators as applicable to certain embodiments of the invention.

Referring to FIG. 1, general features of a portable therapeutic gas concentrator are shown. Typically gas is drawn into the inlet through an inlet filter 1 into a compressor 2. Compressed air is then delivered at a rate of about 3 LPM to 30 LPM (through various filters and other devices) to a gas separation section for selectively adsorbing a component of the gas. The preferred embodiments of the invention, although applicable to a variety of gas concentrator implementations, will be described in detail for the case where the inlet gas is air, and the gas separation section is based on PSA, VSA, VPSA or some combination thereof, utilizing adsorbent beds 3 which selectively adsorb nitrogen, producing oxygen rich product.

A variety of gas separation section cycle types and bed arrangements are known in the art, most of which can benefit from the embodiments of the invention. Whatever the details of the gas separation section 3, typically product gas is accumulated in a storage device 4. Storage devices may include a tank in the traditional sense, or may be some other device effective for holding a volume of gas, such as a tube, or some other volume filled with an adsorbent to increase its holding capacity or even an empty portion of the adsorber itself at the product end of the adsorber. Many modern concentrators used for therapeutic applications also include a programmable controller 5 to operate the concentrator and provide for user interface 8 and communications. Also typical are gas exhaust 6, which may have a vacuum applied in the case of VPSA or VSA systems, and delivery to patient, which often is through a conserver device 7.

Despite the effective moisture mitigative measures described in U.S. Pat. Nos. 7,780,768 and 8,580,015 which might remove 40-98% of water molecules from the feed gas stream, some moisture will remain in the beds 3 when the concentrator is turned off. For the case where there is a desiccant layer, even for a very dry design, the desiccant 11 exists to remove any remaining water as well as other impurities, such as $CO_2$, from the feed gas. During operation impurities are not a significant problem, as the bed 3 is back-purged or evacuated with vacuum periodically in the Adsorption Cycle, thereby not leaving time for moisture and other impurities to diffuse into adsorbent. When the concentrator is not running, particularly for a long period of time, there will be a strong driving force to diffuse for any impurities adsorbed on the pretreatment layer (or feed end of the bed in the case of no pretreatment layer used) or in the gas phase in the void space of the desiccant/adsorbent at the feed end of the bed. If the concentrator is not sealed to the outer atmosphere via a valve on the exhaust contaminants can diffuse either to the outer atmosphere (likewise other contaminants can diffuse into the beds) or the contaminants can diffuse into the active "clean" section of the bed(s). If the concentrator is sealed to the outer atmosphere via a valve, any impurities present will diffuse into the bed only. Pretreatment layers are often selected due to their ease of regeneration during process cycles relative to that for the contaminants in the active separation layer. Thus during shutdown conditions the result can be a material with a low affinity for a given contaminant adjacent to a material with a high affinity for a given contaminant, and a large gradient in chemical potential for the contaminant provided sufficient treatment of the feed gas has taken place. Given the complex array of components required to prevent the contamination of zeolite while a portable oxygen concentrator is running and while it is in storage, the inventors devised a way to treat the sieve beds as a semi-disposable item so that they can be readily replaced rather than protected or overdesigned to achieve the required device service life of the system as a whole.

While it is known in the art to make the zeolite beds easily serviced, there have been no successful designs that minimize the number of replacement components and simultaneously retain the ability for the patient to easily change the sieve In some embodiments, a common member may be disposed at one end of the two adsorbers and may include at least one of the input or output ports. In other embodiments an additional common member may be disposed at the other end of the two adsorbers. In some embodiments the additional common member may contain at least one of the input or output ports. In other embodiments the common member may form a portion of the adsorber seal. In other embodiments the adsorber may contain a flared edge that forms an additional portion of the adsorber seal. In some embodiments the seal may be clamped in place by an additional common member. In other embodiments the seal may be a face seal between the common member and the adsorber column. In some embodiments the adsorbers may be configured with dimensions to at least one of minimize the width of the two attached adsorbers or minimize the length of the two attached adsorbers. In some embodiments the adsorbers when mated with the platform are accessible from the exterior of the platform.

The invention herein requires a concentrator to be designed from the ground up around the concept of a field replaceable sieve bed. The sieve beds must be easily removed from the system, yet still retain their air-tight sealing mechanisms and robust resistance to shock, drop, and vibration. In medical oxygen concentrators, and particularly portable oxygen concentrators currently in the marketplace, access to the sieve beds typically requires removal of several outer housing components, tubing connections, fittings, screws, and other hardware components. These designs are simply unsuitable for field service by the user of the oxygen concentrator.

Figure 2:
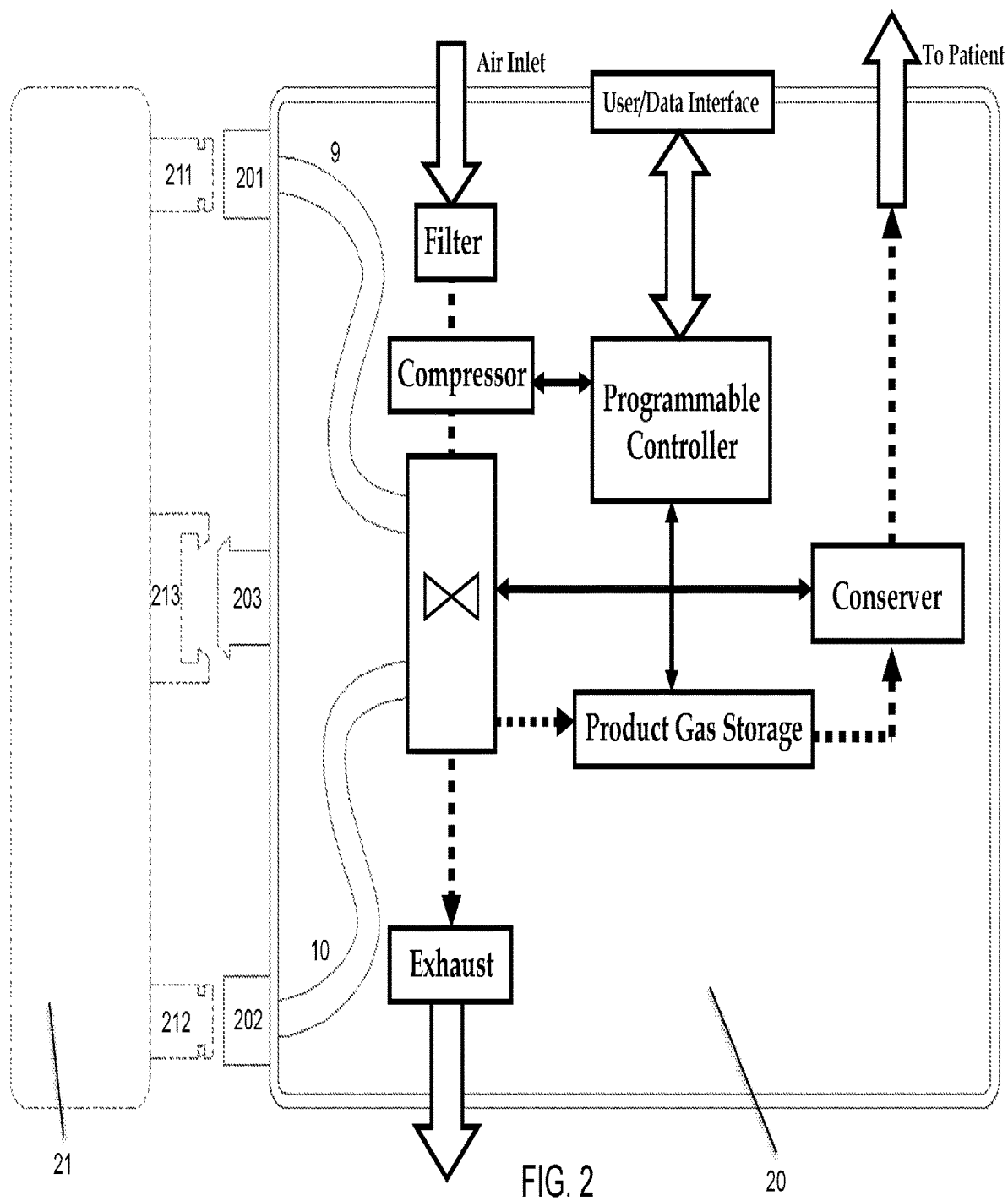
FIG. 2 illustrates the general concept where the concentrator platform is one portion and the user replaceable adsorber is another portion of a complete concentrator.

A particularly effective embodiment of the invention is a portable oxygen concentrator where the sieve bed cartridges or adsorbers can be removed and replaced without removing the outer housing or any fasteners of any kind. FIG. 2 illustrates a preferred embodiment where inlet and outlet gas connections 201 and 202 are located externally to a concentrator platform section 20, containing the concentrator elements other than the adsorber beds, to allow for easy field replacement of adsorber 21 with inlet and outlet ports 211 and 212 respectively. Further, the adsorbers are robustly attached to core platform 20 to withstand the necessary shock, vibration, and impact a portable oxygen concentrator may endure via retention mechanism components 203 and 213. By locating the adsorbers 21 outside of the platform 20, the integrity of the concentrator assembly 20 is not compromised by being accessed by the user who would not have adequate training to perform maintenance on internal components of the platform 20. The receptacle ports 201 and 202 are preferably connected to the air valves by compliant members 9 and 10.

Figure 3A:
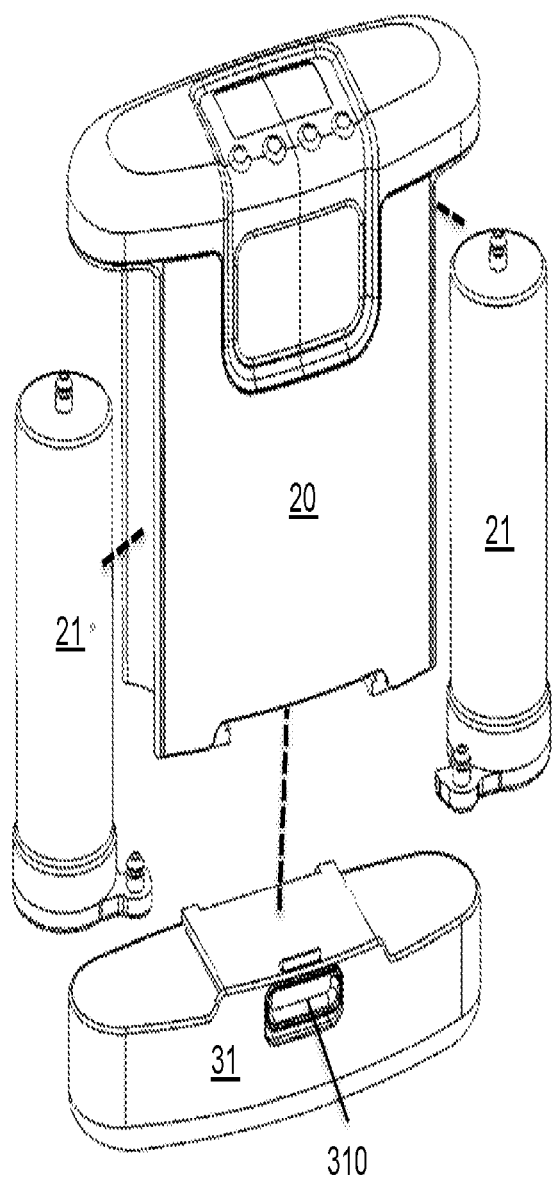
FIGS. 3A and 3B illustrate the concentrator sections in both an unassembled and assembled state.
Figure 3B:
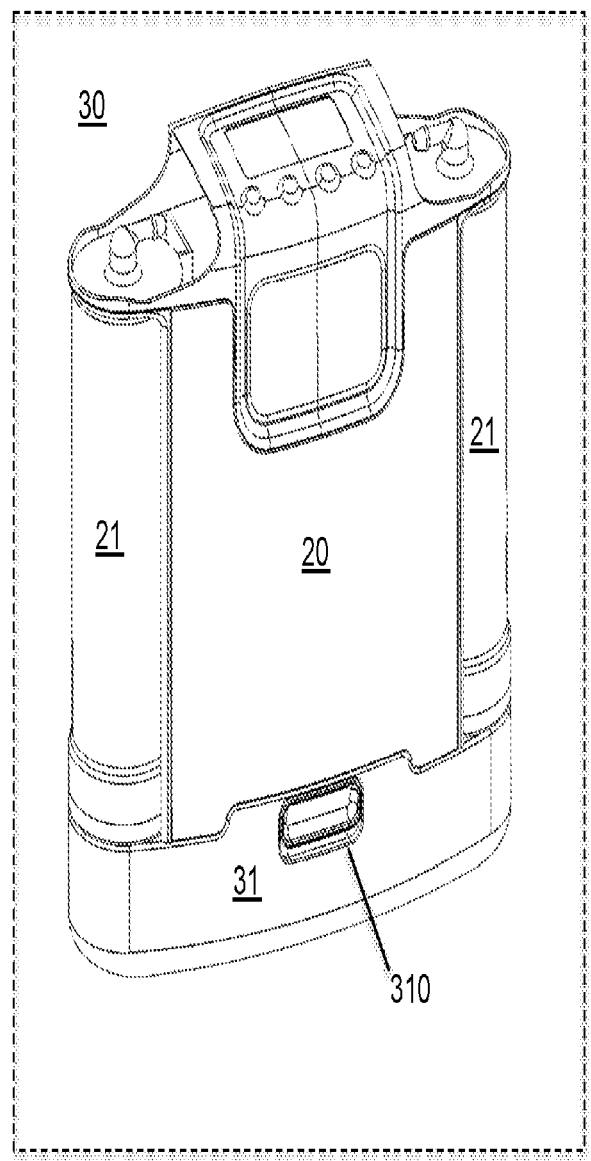
Figures 4A, 4B:
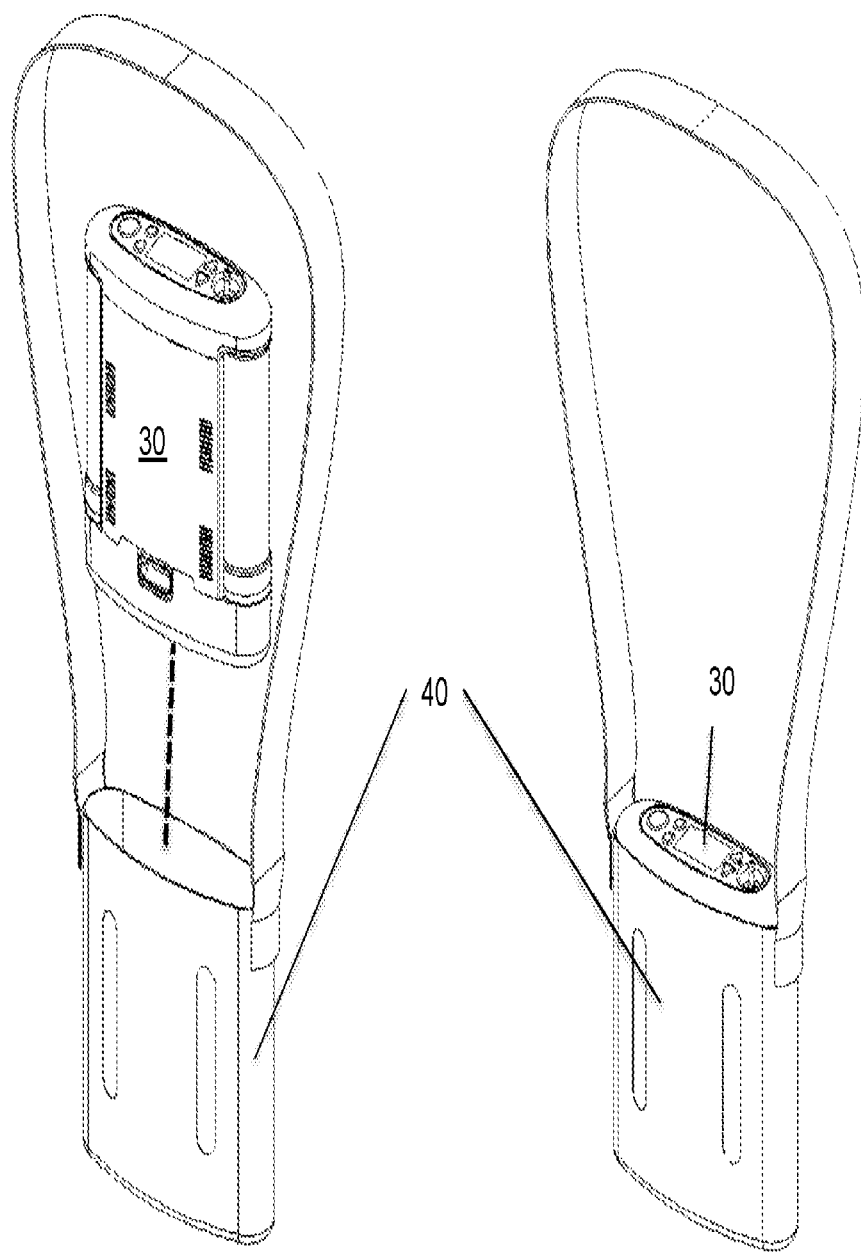
FIGS. 4A and 4B illustrate an assembled concentrator in a case.

A portable concentrator with sieve beds designed for field service is substantially different than a typical portable oxygen concentrator. The design for patient service changes the layout of the concentrator so that operational components of the system are accessible to the patient by being located external to the concentrator housing. While this change facilitates the patient servicing of the system, it also poses aesthetic challenges to the designer since the portable concentrator is used outside the home and must not look out of place while being carried by a patient. Therefore, it is an objective of the present invention to seamlessly integrate the adsorbers into the industrial design of the concentrator so that they remain accessible, but appear to blend in with the overall design of the concentrator. In a preferred embodiment shown in FIGS. 3A and 3B the adsorbers 21 form the sides of the concentrator while the battery 31 forms the bottom of the concentrator. FIGS. 3A and 3B further depict a mechanical advantage designed by the inventors to use the mechanically robust battery 31 and battery latching mechanism 310 to reinforce the retention of the adsorbers and to prevent inadvertent release of the adsorbers during operation. To remove the adsorbers 21 for the purpose of exchanging them, the user would first remove the battery to access the adsorber release mechanisms 203/213. The entire system 30 is then preferably mounted inside a carrying case 40 to enable portable use by the user (FIGS. 4A and 4B).

Figures 5A, 5B:
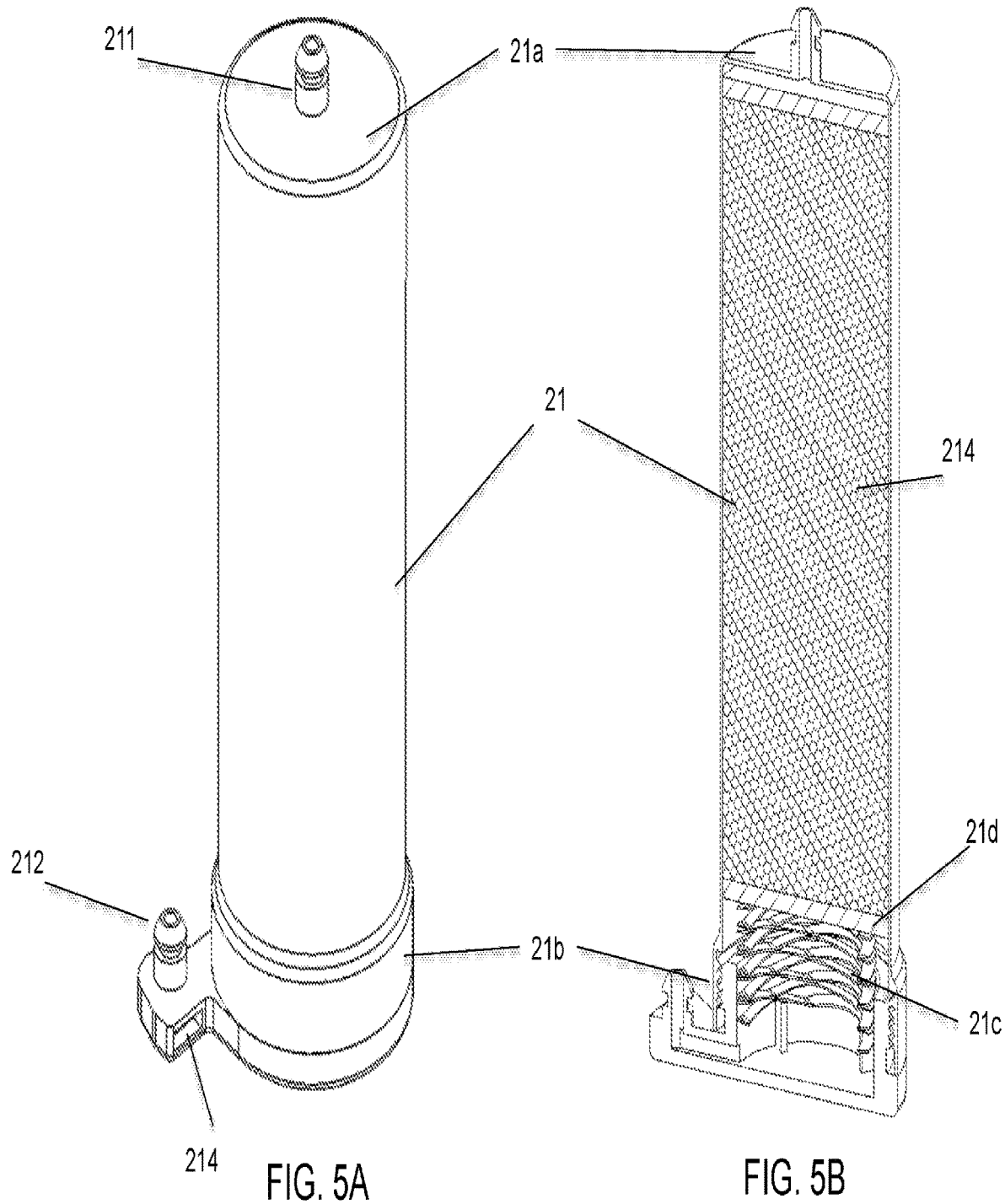
FIGS. 5A and 5B depict an exemplary user replaceable adsorber.

FIGS. 5A and 5B depict a preferred embodiment of the adsorber designed by the inventors. The adsorber is built as an independent unit and can be pneumatically interfaced to the platform 20 via inlet and outlet ports 211 and 212 while being mechanically interfaced to the concentrator via retention receptacle 214. The internal components of the adsorber 21 are similar to other adsorbers found in portable oxygen concentrators designed by the inventors. The adsorbers contain a nitrogen selective adsorbent 214, porous frits 21d to retain the adsorbent and springs 21c to prevent the adsorbent from moving and breaking down during pressure cycling that is typical with a PSA system. The preferred embodiment 21 shows the column cap 21b being threaded into the column 21. This embodiment allows the external surfaces of the adsorber to be smooth and free of fasteners or retainers that would otherwise pose a hazard to the user while exchanging the adsorbers in the concentrator. Further, the threaded engagement of the cap to the column ensures that the contaminated adsorbers can be returned to the factory for replacement of the adsorbent, thus further reducing the cost of the adsorber exchange. The cap could alternatively be permanently affixed to the column by rolling the edge of the column over the cap for retention or using adhesive to seal the two parts together, but these methods make the adsorber a throw-away item which creates waste. The preferred embodiment designed by the inventors allows only the adsorbent or adsorbents to be discarded during an adsorber refurbishment at the factory.

Figures 6A, 6B, 6C:
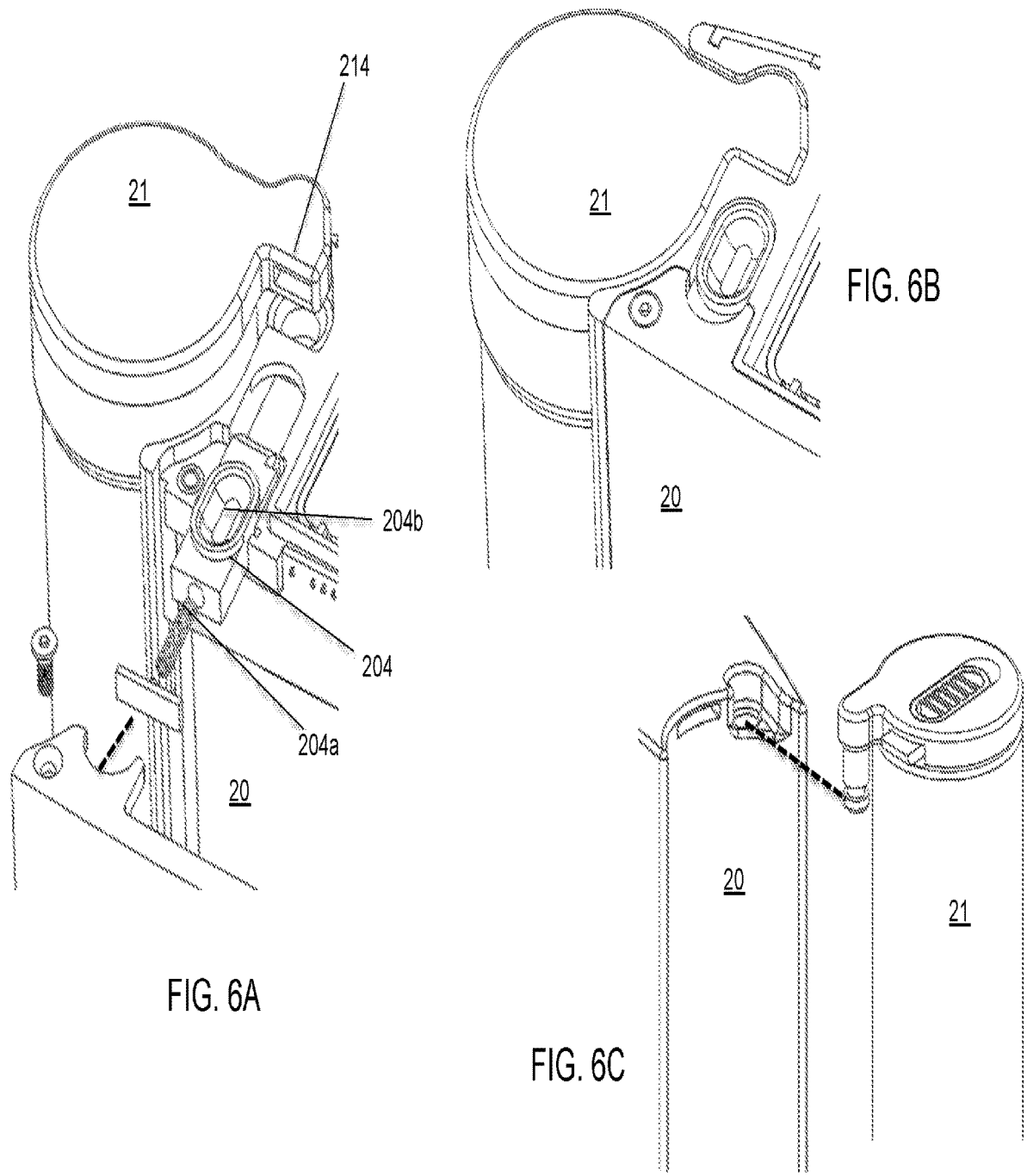
FIGS. 6A, 6B, and 6C depict one example of a suitable user actuatable adsorber retention mechanism.
Figure 7A:
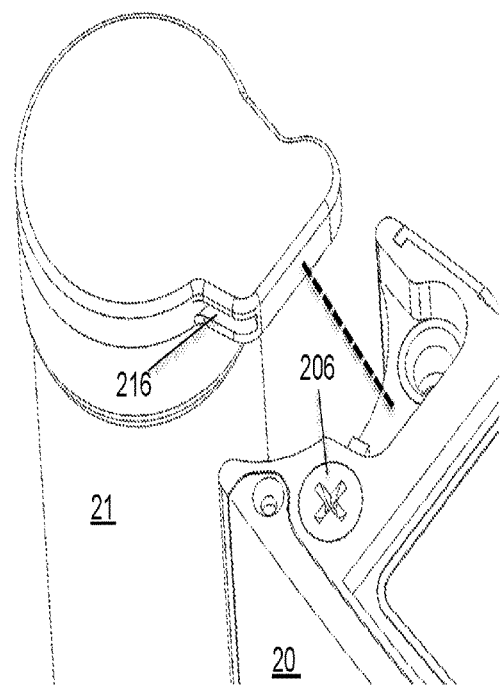
FIGS. 7A, 7B, 7C, and 7D depict another example of a suitable user actuatable adsorber retention mechanism.
Figure 7D:
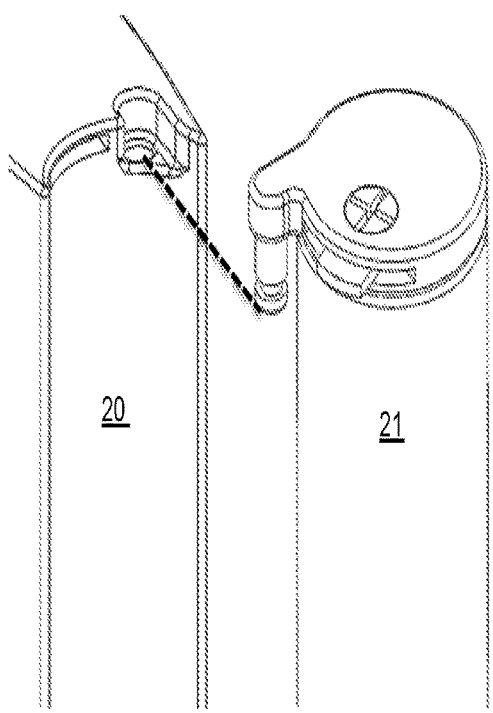
Figures 7B, 7C:
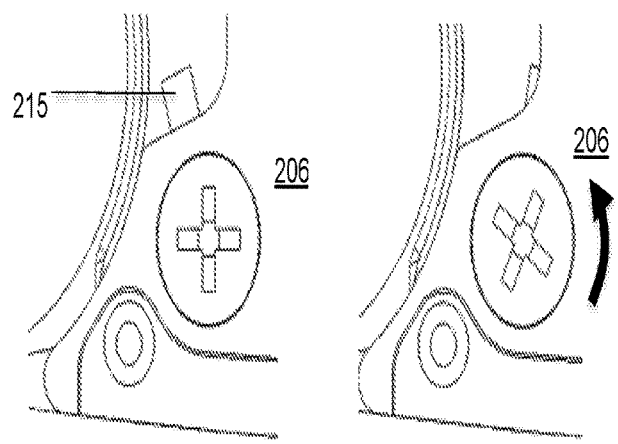

A further objective of the inventors was to develop an appropriate latching mechanism that would securely hold the adsorbent vessels sealed to the concentrator, but also allow for easy replacement by the patient. FIGS. 6A, 6B, and 6C depict an exemplary latching mechanism comprised of a receptacle 214 on the adsorber and a retention plunger 204 on the platform 20. The latching plunger 204 is held in place by spring force applied by spring 204a. The latch is disengaged by the user by sliding the engagement button 204b away from the column latch receptacle 214. The force applied by spring 204a must be sufficient to prevent inadvertent disengagement of the latch, but also low enough to be easily disengaged by the users' finger without a painful or difficult effort on the part of the user. The inventors have found that a disengagement force of approximately 10-25 Newtons meets both of these requirements. As shown in the Figure, the location of the mechanisms could be switched between the adsorber and platform, but it is generally preferable to keep the cost and complexity as low as possible for the replaceable adsorber, so the latching hardware on the platform is preferable.

FIGS. 7A, 7B, 7C, and 7D depict an alternative embodiment of the invention where the retainer 216 is engaged by locking tab 215 via the rotation of locking screw or knob 206. Reverse rotation of the locking screw or knob 206 disengages the locking tab 215 allowing the adsorber to be removed. This design includes the advantage of not requiring a spring to maintain the retention of the adsorber, but the rotational design also may require a common tool such as a Phillips screwdriver or Torx driver to remove or install the adsorbers. Requiring a tool for removal or installation of the adsorbers might be an advantage in some usage scenarios or a disadvantage in other usage scenarios. The inventors designed the concentrator system to allow for these differing usage scenarios so that the optimal latching and retention mechanisms may be chosen accordingly. As for the embodiment of FIGS. 6A, 6B, and 6C, the placement of the mechanisms could be reversed as shown, but the placement of the rotating tab on the platform is preferable.

Figure 8:
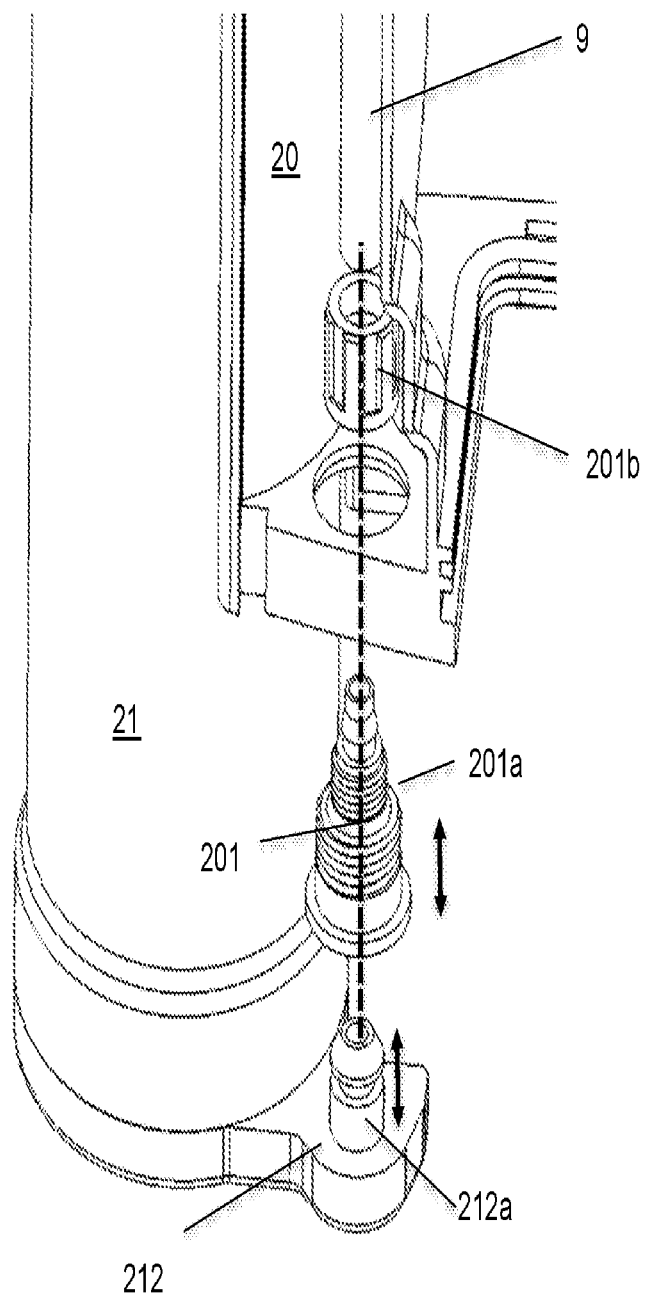
FIG. 8 depicts a port seal for a replaceable adsorber where the port is independently mounted from the platform chassis.

As in any manufacturing operation, there will be variations in the dimensions of all components of the system, so the user replaceable adsorbent must contain a significant amount of sealing overlap to prevent inadvertent leakage that would degrade the system's performance. Referring to FIG. 8, in a particular embodiment, the inlet and outlet connections 211 and 212 must therefore contain overlapping sealing elements that allow for some positional compliance without sacrificing the quality of the sealing of the pneumatic connections. This compliant sealing mechanism is achieved by using an o-ring on the adsorber and a vertical bore 201a on the receptacle 201 that creates a seal along its entire length, thus allowing between 1 and 5 millimeters of vertical compliance to the seal. This compliance allows for some variation and compliance in the latch as well as some variation in the height of the column components that would be seen in a typical manufactured component. Further, FIG. 8 depicts the gas receptacle 201 as a modular component that is independent of the platform 20. This is accomplished by connecting adsorber receptacle port 201 directly to compliant member 9, with a locking mechanism 201b. Thus platform 20 is used to locate the port 201, but they are not a shared structure. By decoupling the pneumatics from the structural elements of the system, the pneumatics are protected from the adverse affects of drop or impact. In the extreme case when platform 20 housing components are broken during impact or drop, port 201 may likely stay connected to member 9 and column inlet or outlet fitting 212a. Thus the pneumatic system integrity may be maintained by adhering to the modular gas connector system 201 and 212 as shown in FIG. 8 even in the event of damage to the core system 20.

FIGS. 9A, 9B, 9C, and 9D depict an alternate latching mechanism that utilizes push button adsorber release buttons 207 to disengage the latching mechanism 207b and 207c and release the adsorbers 21. Again, the spring 207a must exert an optimal force of about 10 to 25 Newtons on the latching mechanism to sufficiently secure the adsorber 21 during use and pressure cycling while still enabling the finger of the user to overcome the spring force and release the adsorber 21 without discomfort or difficulty.

Figures 10A, 10B:
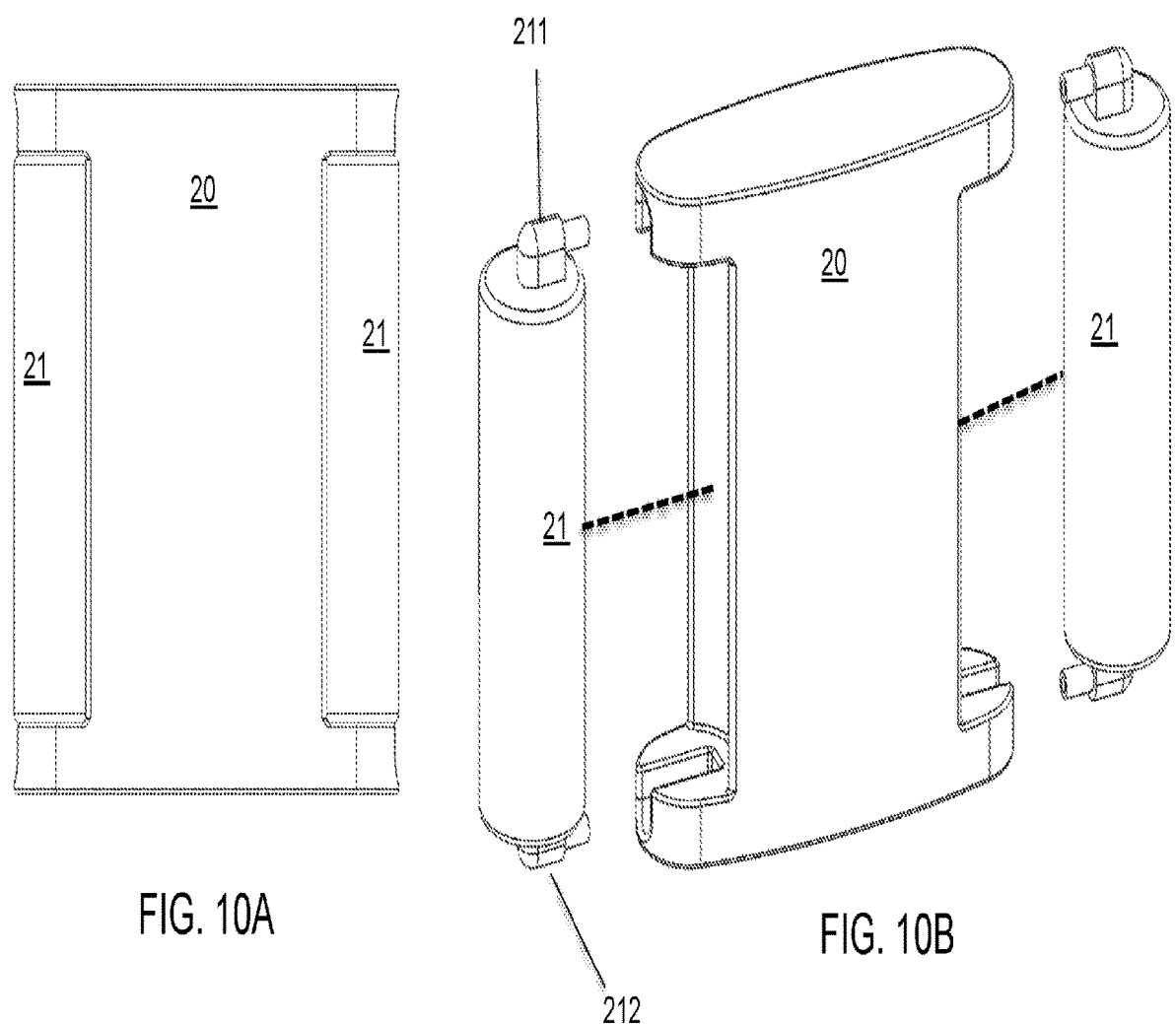
FIGS. 10A and 10B depict an alternative port geometry.
Figure 11A:
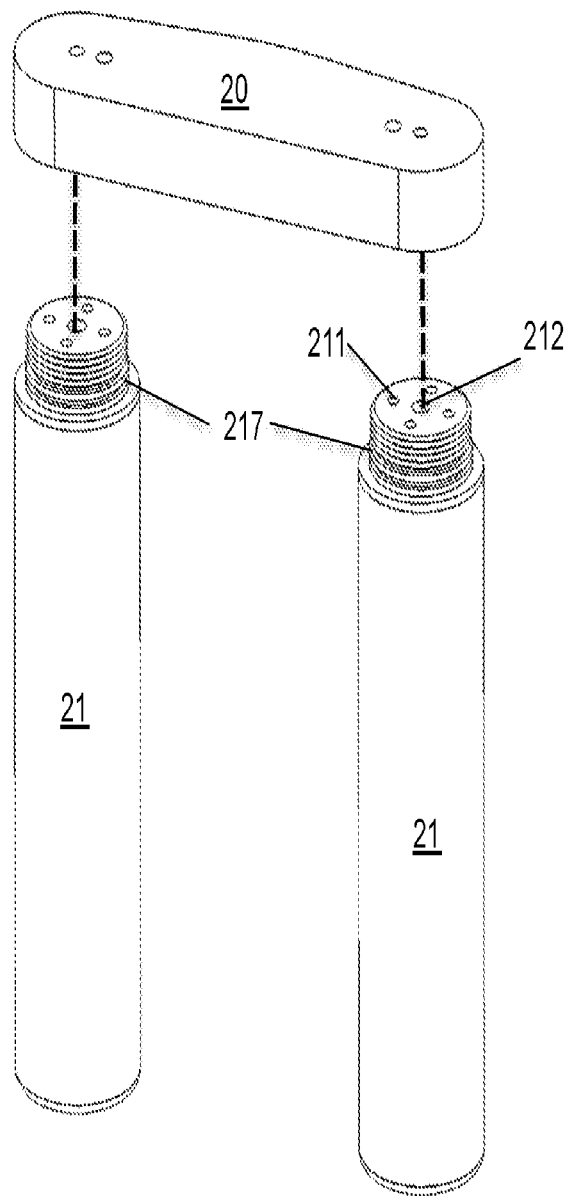
FIGS. 11A and 11B depict an arrangement where user replaceable adsorbers are installed with a threaded interface.
Figure 11B:
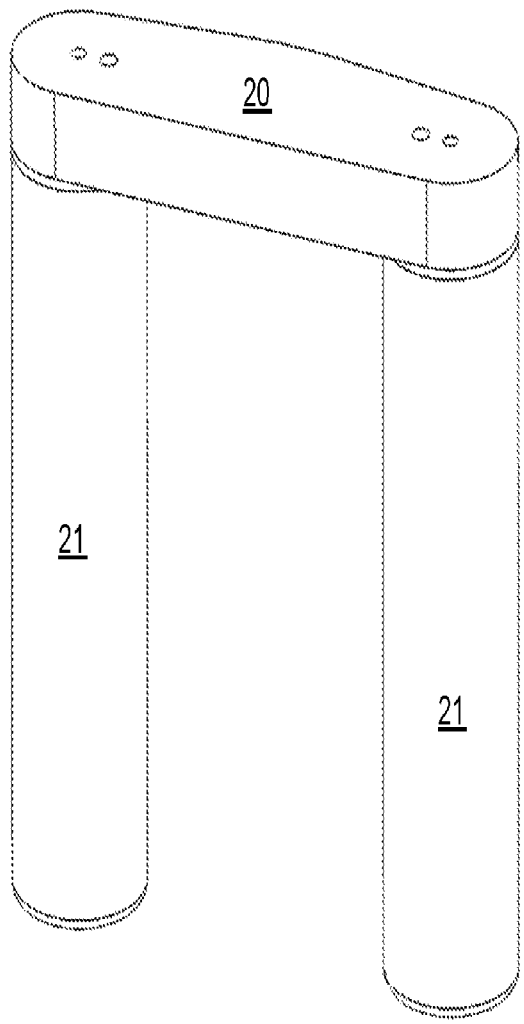
Figure 12A:
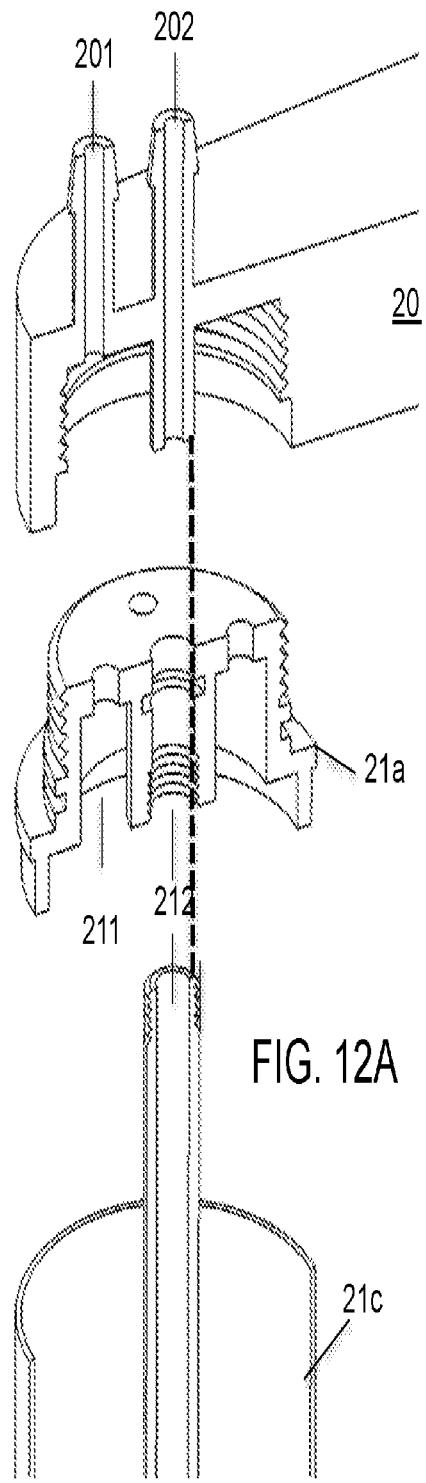
FIGS. 12A and 12B depict details of the threaded interface.
Figure 12B:
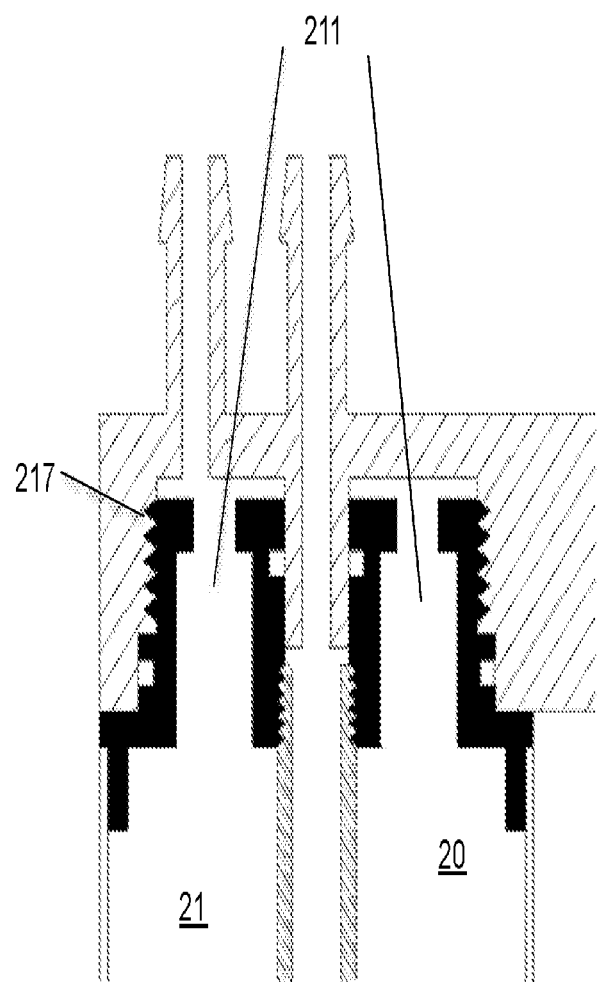

FIGS. 10A and 10B depict another alternate embodiment of the invention where the axis of insertion of the inlet and outlet ports 211 and 212 are perpendicular to the axis of flow of gas through the adsorber 21. This embodiment simplifies the design by utilizing the same gas connections at the inlet and the outlet port, but does not have the advantage of being able to utilize the battery as a redundant retention mechanism during use.

The coaxial threaded adsorbers 21 in FIGS. 11A, 11B, 12A and 12B are another embodiment of the invention where both gas inlet and gas outlet ports 211 and 212 are coaxial and located at the same end of the adsorber by utilizing an integral return tube to retrieve gas from the opposite end of the column. The engagement and retention threads 217 create the mechanically robust connection between adsorber 21 and platform 20 while the pneumatic connections 211 and 212 are radially sealed by o-rings with sufficient vertical overlap to allow adsorber 21 to seal in any rotational orientation such that rotational position or timing is independent from the sealing. Adsorber endcap 21a is threaded onto return tube connection 212 to seal the return tube. Adsorber endcap is then sealed to column 21c in any rotation by any number of possible sealing methods such as an o-ring or face seal gasket. The entire adsorber including column 21c and endcap 21a then mate to core section 20 to form a complete portable oxygen concentrator. The rotational independence ensures that user replacement of the adsorber and the variable tightening torque applied by the user will not create detrimental leaks at the inlet and outlet gas connections.

Figure 15A:
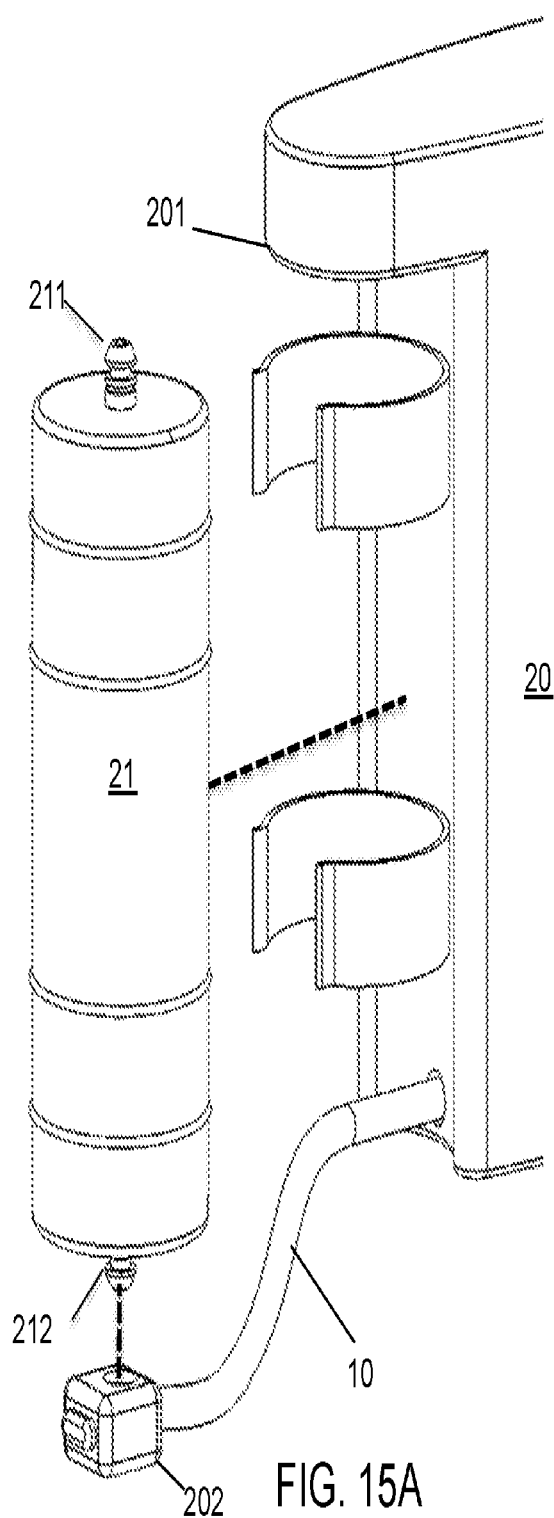
FIGS. 15A and 15B depict another example of a suitable user actuatable adsorber retention mechanism.
Figure 15B:
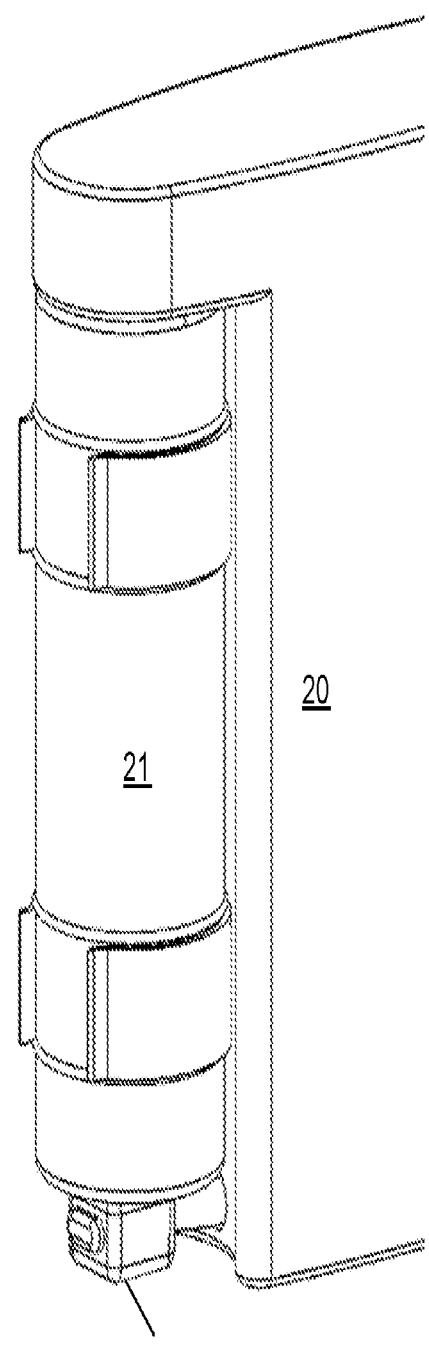

The alternate embodiment of the invention depicted in FIGS. 13A and 13B utilize a twist-lock mechanism to lock the adsorber 21 to the platform 20. Progressively engaging locking tab 218 draws adsorber 21 into the receptacle located in platform 20 and is ideally employed in combination with the coaxial adsorber design where both inlet and outlet ports 211 and 212 are collocated at a single end of the adsorber. Alternatively, one of the inlet or outlet ports may be located at the opposing end of the adsorber 21 and the gas connection may be made with a flexible tubing element 10 as depicted in FIGS. 15A and 15B.

Figure 14A:
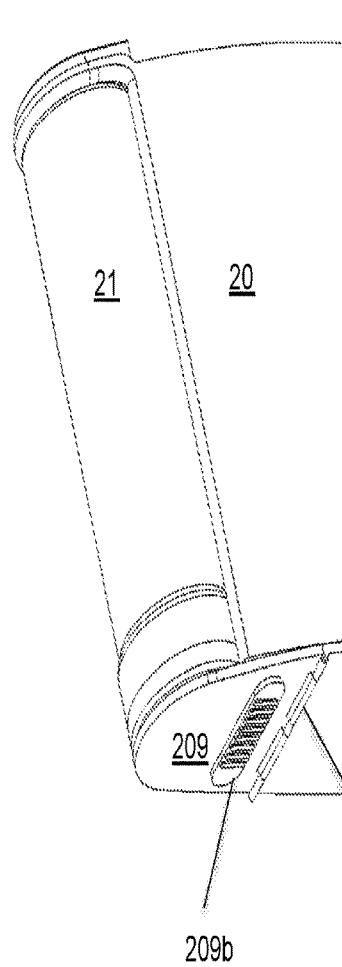
FIGS. 14A, 14B, and 14C depict another example of a suitable user actuatable adsorber retention mechanism.
Figure 14B:
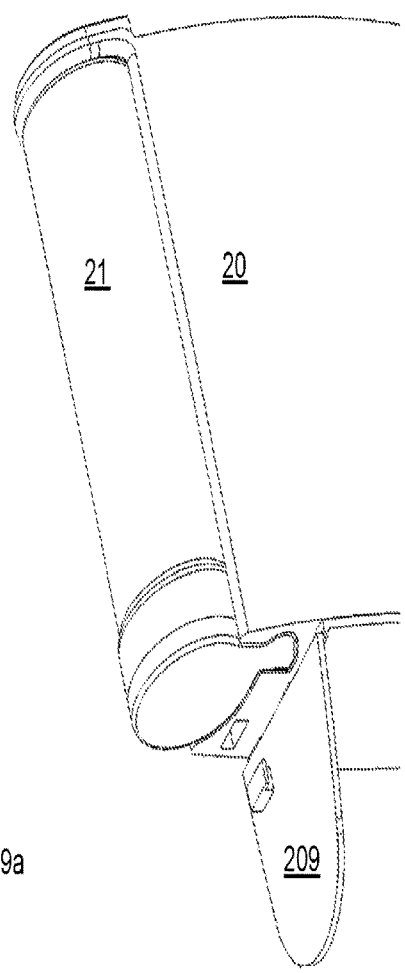
Figure 14C:
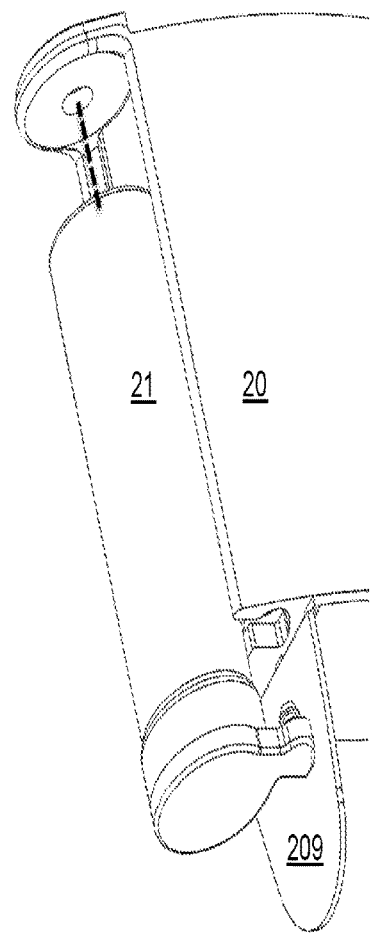

Yet another alternate embodiment of the user replaceable adsorber is depicted in FIGS. 14A and 14B. In this embodiment, adsorber 21 is held in place to platform 20 by a hinged floorplate 209 such that no retention elements at all are required on the adsorber 21. In this embodiment the hinge 209a and the latch 209b are both mounted on the platform 20 such that floorplate prevents the adsorber from disengaging from the platform 20 when latched in the closed position by latch 209b.

Figure 16A:
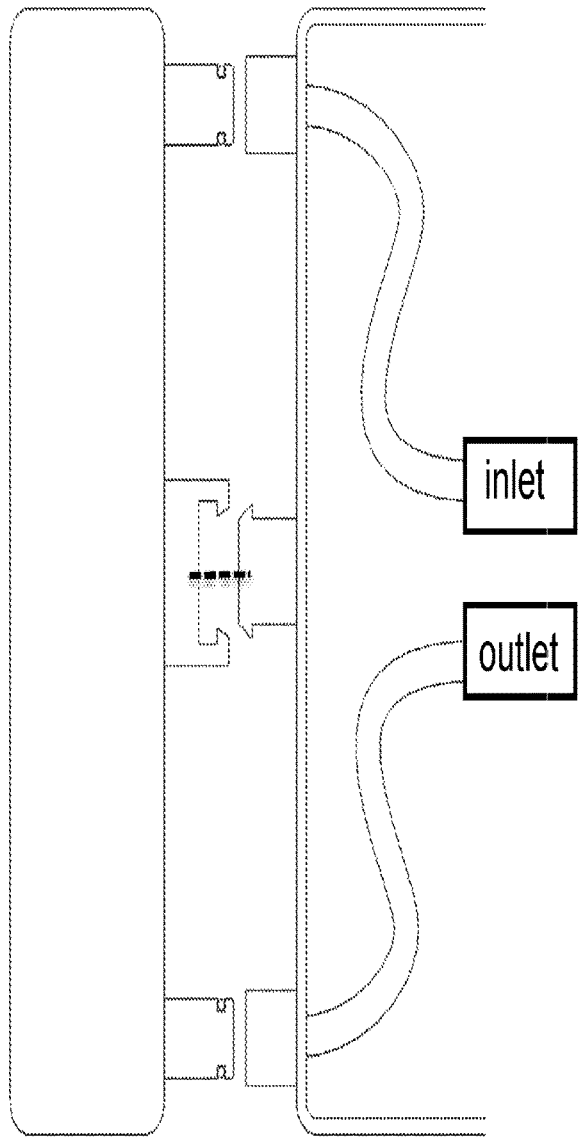
FIGS. 16A and 16B show that alternative inlet and outlet port arrangements are possible.
Figure 16B:
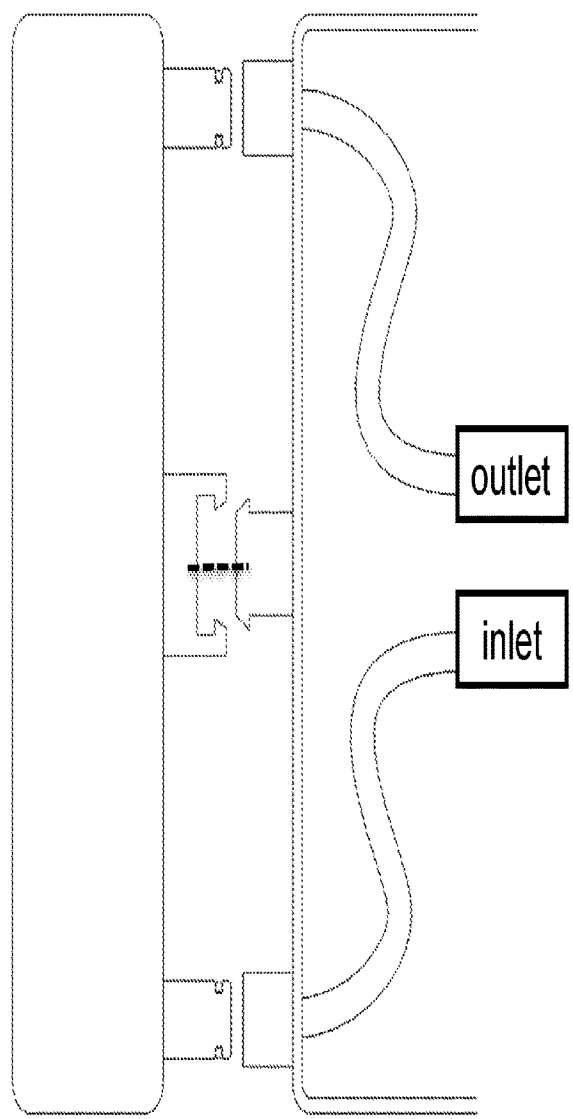
Figure 17A:
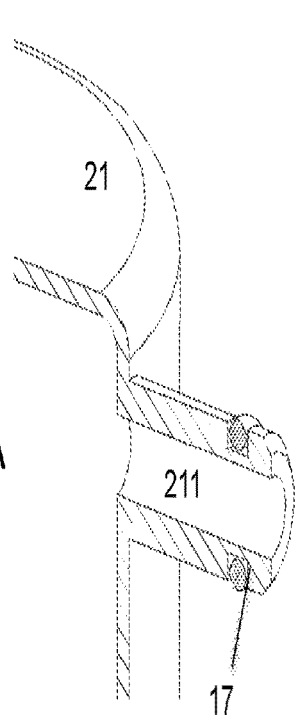
FIGS. 17A, 17B, 17C and 17D depict a variety of radial seal arrangements.
Figure 17B:
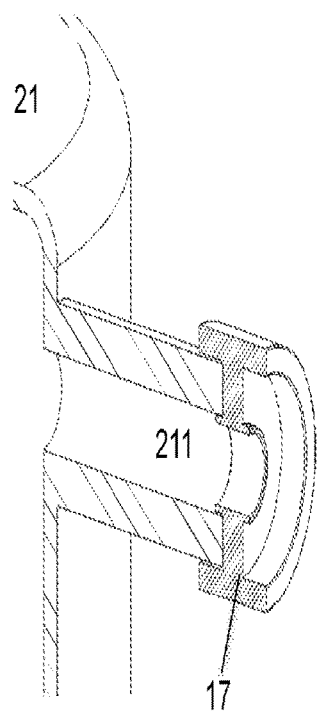
Figure 17C:
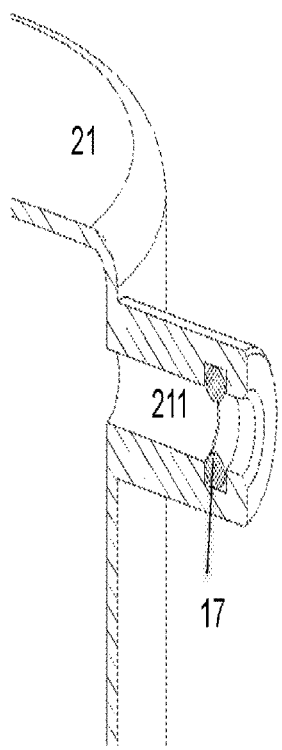
Figure 17D:
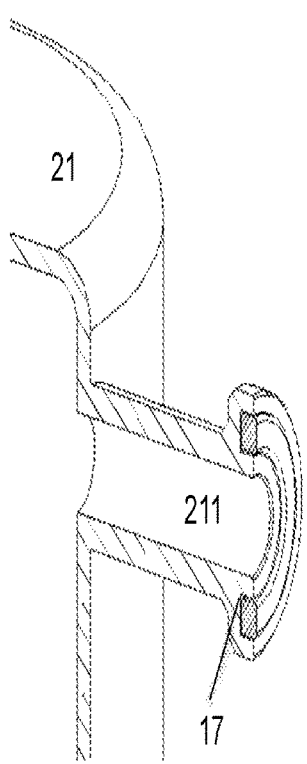

The specific definition of the inlet and outlet ports on adsorber 21 are merely chosen by convention and can be reversed in any embodiment as depicted in FIGS. 16A and 16B. A typical adsorber as designed by the inventors utilizes a larger inlet port where feed gas enters the column to prevent power losses caused by flow restriction and a smaller port on the product end or outlet where the oxygen exits the adsorber or enters the adsorber during the purge step of the PSA cycle. In constructing the adsorber, the feed or inlet end of the adsorber may be further defined when a layered adsorbent system is utilized and a pretreatment layer is used to remove contaminants from the feed stream prior to the exposing the main layer adsorbent to the feed stream.

Inlet and outlet ports and receptacles 201 and 211 may utilize a variety of well established sealing elements as depicted in FIGS. 17A, 17B, 17C, and 17D. Sealing element 17 is ideally a compliant o-ring made from one of several compounds such as rubber, viton, or silicone. Alternately, the sealing element 17 may be a custom face sealing gasket also made of rubber, viton, or silicone, but this embodiment may lack the necessary compliance to produce a repeatable and robust seal as part tolerances vary in a high volume production environment.

Figure 18A:
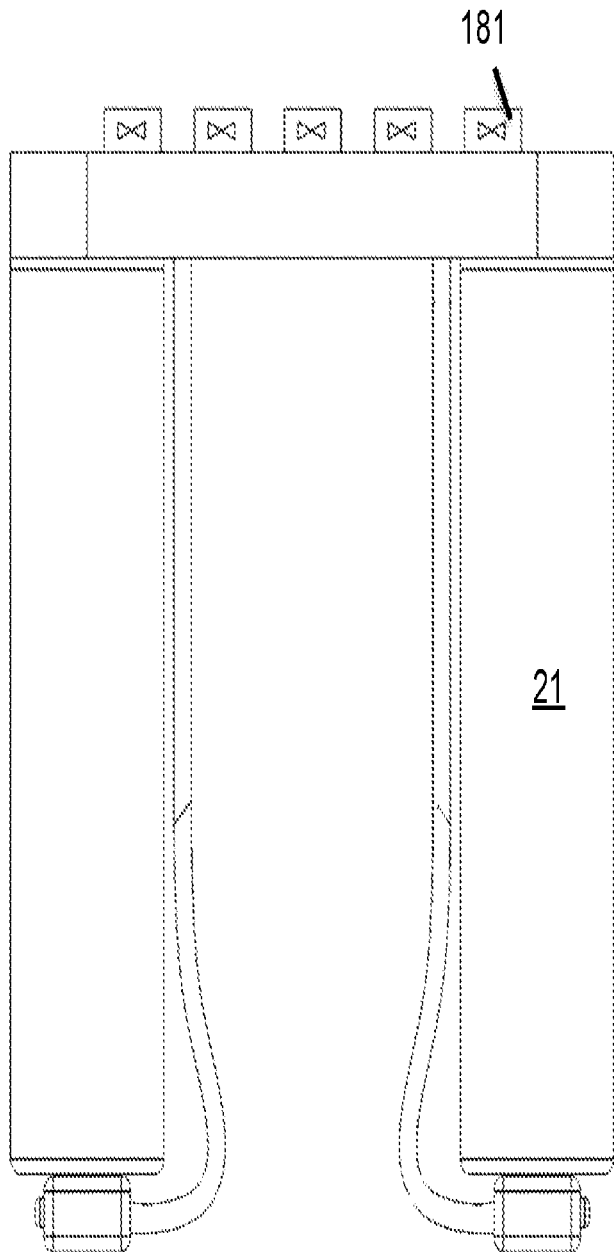
FIGS. 18A and 18B show an embodiment where one or more of the gas connections may be directly to a manifold.
Figure 18B:
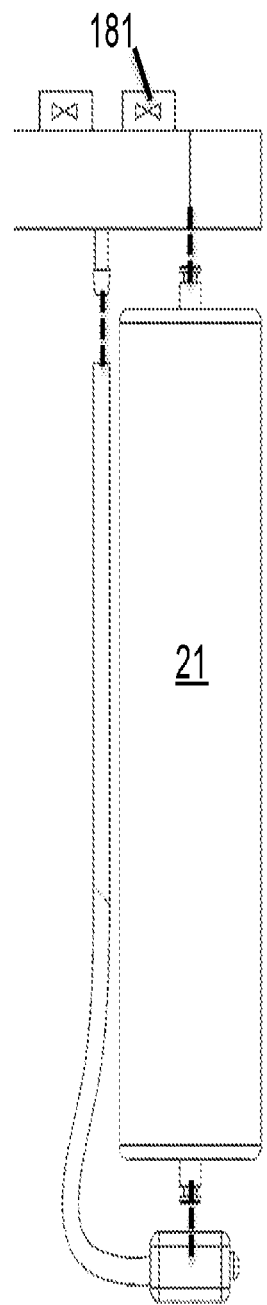

Although the preferred approach to connect the adsorber/receptacle ports to the platform internal valving is by compliant member for increased resistance to shock, it is certainly possible to make one or more these connections by having the receptacle ports connect directly to a manifold. Such an arrangement is shown by way of example where one port of adsorber 21 connects directly to manifold 181 as shown in FIGS. 18A and 18B.

It may be convenient in some embodiments, to mount the adsorbers next to each other in platform 20, and to attach the adsorbers together, so that the placement of both adsorbers is facilitated to be easily performed in one operation and to potentially minimize part count by utilizing parts that serve as common structural and pneumatic components. Several versions of two adsorbers attached and mounted adjacent to each other are possible within the teachings of this disclosure.

Figure 19A:
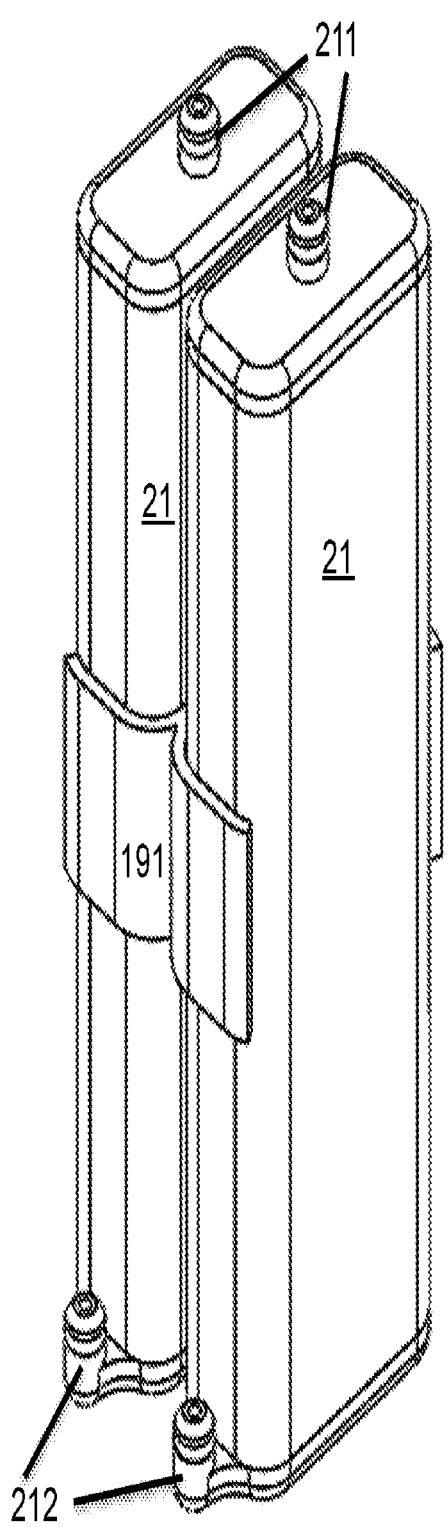
FIGS. 19A and 19B show illustrative embodiments of co-attached adsorbers.
Figure 19B:
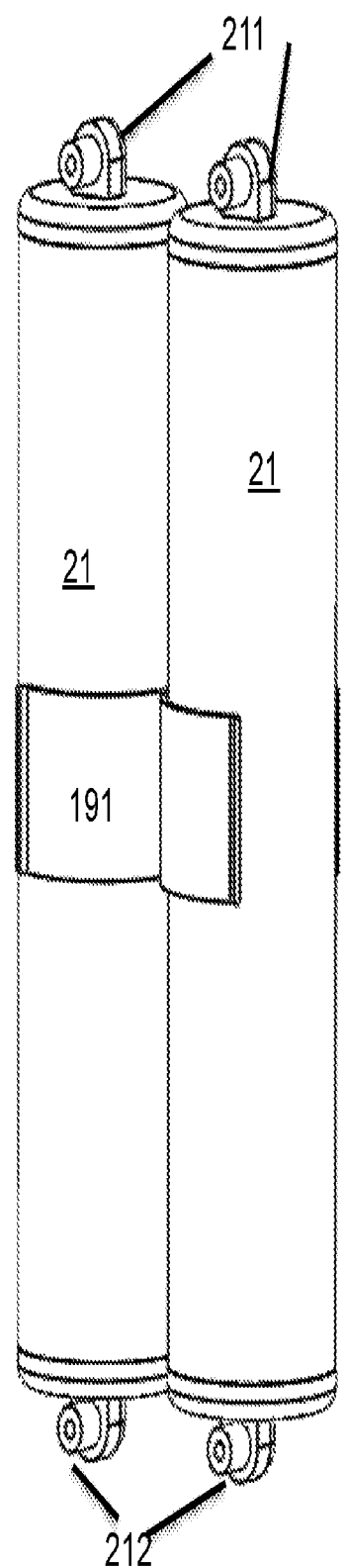

FIGS. 19A and 19B show adsorbers 21 held together with one common member 191, which both attaches the adsorbers together and holds them with all ports 211 and 212 aligned for mounting. FIG. 19A shows the ports 211 and 212 on each end of adsorbers 21 in the configuration where the inlet and outlet flow is substantially along the same axis as the flow axis of the adsorbers. This configuration is a co-mounted version of the arrangement shown in FIGS. 5A and 5B, with different mounting embodiments shown in FIGS. 6 to 9. FIG. 19B shows the ports 211 and 212 on each end of adsorbers 21 in the configuration where the inlet and outlet flow is substantially perpendicular to the flow axis of the adsorbers. This is a co-mounted version of the configuration shown in FIGS. 10A and 10B. To show the various possibilities for co-mounted adsorbers FIG. 19A shows curved rectangular adsorbers while FIG. 19B shows round adsorbers such as are shown in the earlier Figures. Other shapes, such trapezoids, ovals, D-shaped, and combinations thereof, as are possible and fall within the claimed scope of this application. The appropriate shape for an adsorber may be determined by the design of the platform 20 as well as the size, wall thickness, and operating pressure of the adsorber to ensure structural integrity.

Figure 20A:
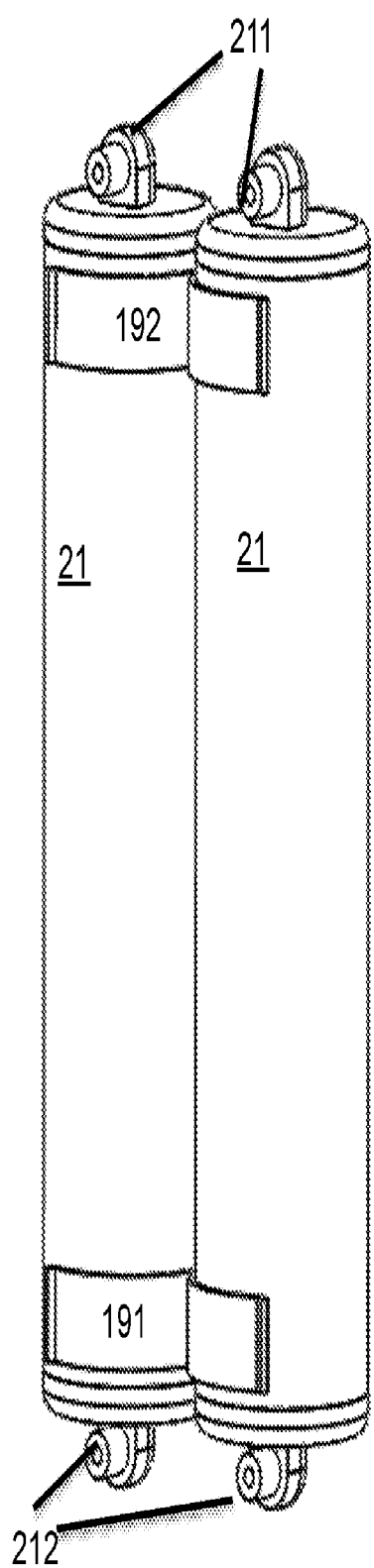
FIGS. 20A and 20B show illustrative alternative embodiments of co-attached adsorbers.
Figure 20B:
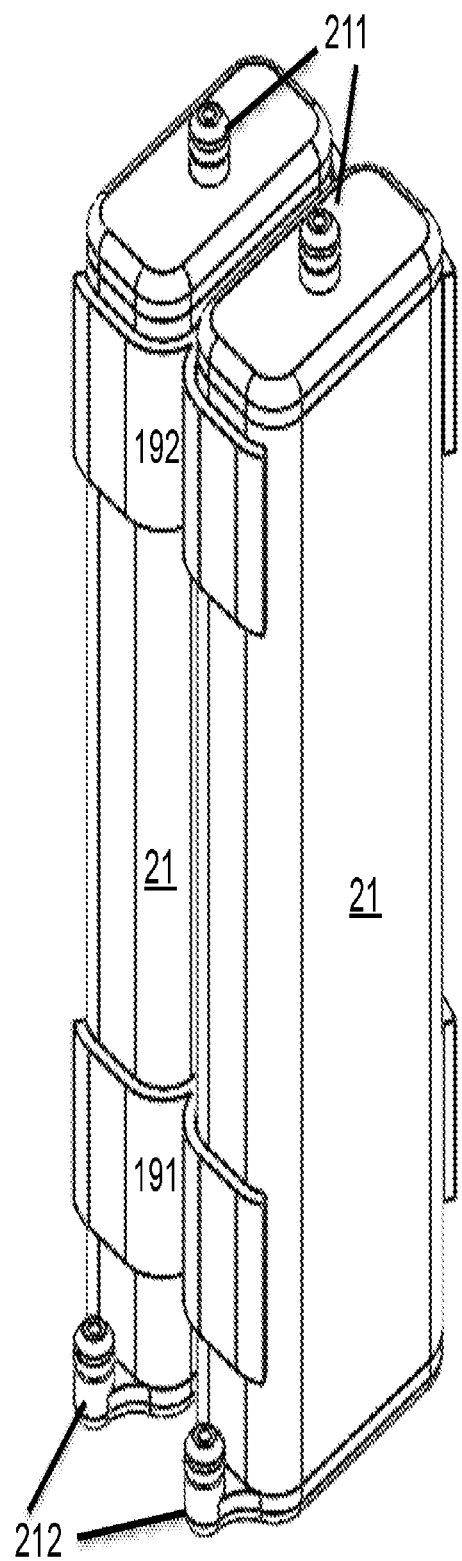

FIGS. 20A and 20B show adsorbers 21 held together with two common members 191 and 192, which both attach the adsorbers together and holds them with all ports 211 and 212 aligned for mounting. FIG. 20A shows the ports 211 and 212 on each end of adsorbers 21 in the configuration where the inlet and outlet flow is substantially perpendicular to the flow axis of the adsorbers. This is a co-mounted version of the configuration shown in FIGS. 10A and 10B. FIG. 20B shows the ports 211 and 212 on each end of adsorbers 21 in the configuration where the inlet and outlet flow is substantially along the same flow axis of the adsorbers. This configuration is a co-mounted version of the arrangement shown in FIGS. 5A and 5B, with different mounting embodiments shown in FIGS. 6 to 9. Again both round and rectangular adsorbers are shown by way of example.

Figure 21A:
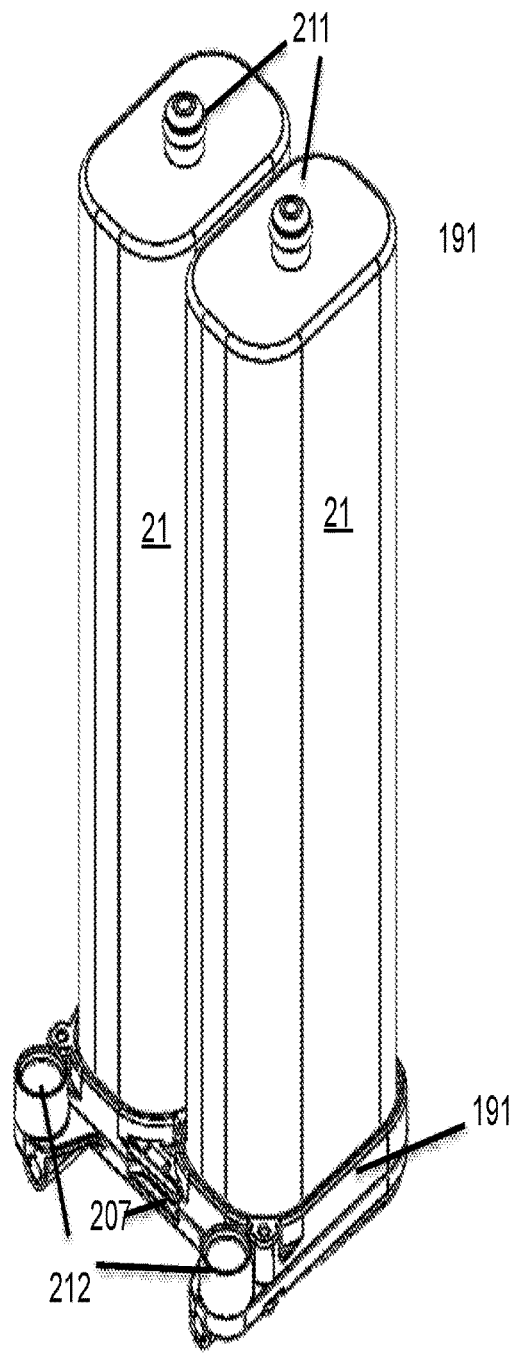
FIG. 21A shows an illustrative embodiment of co-attached adsorbers with a common member including ports and FIG. 21B shows the embodiment of FIG. 21a mounted in the platform.
Figure 21B:
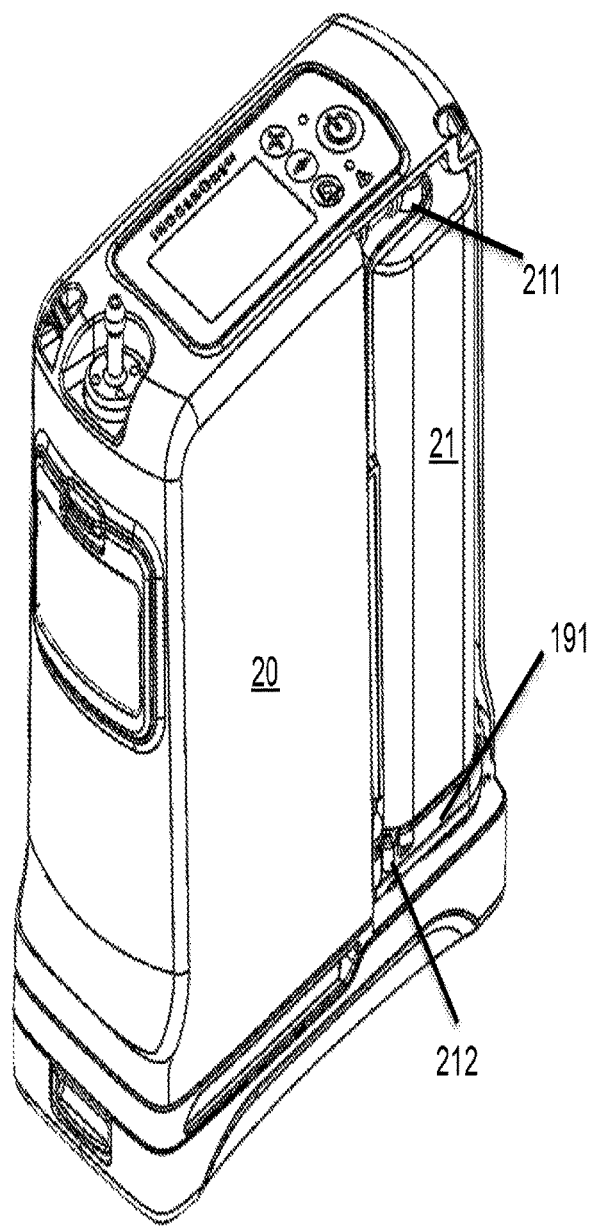

FIG. 21A shows adsorbers 21 held together with one common member 191, which both attaches the adsorbers together and holds them with all ports 211 and 212 aligned for mounting. FIG. 21A shows the ports 211 and 212 on each end of adsorbers 21 in the configuration where the inlet and outlet flow is substantially along the same axis as the flow axis of the adsorbers. Common member 191 also includes the ports 212. Ports 212 are formed into common member 191 and sealed to the adsorbers 21 in a variety of ways, some of which will be shown below. FIG. 21B shows the embodiment of FIG. 21A mounted into platform 20 where the rectangular shape of the adsorbers 21 are used to minimize the width of the platform 20 compared to a round adsorber. The rectangular length to width ratio of the adsorber is approximately 1.5 to 1 to allow the completed concentrator to be narrower than two circular adsorbers of equivalent cross section would allow. The rectangular shape with flat sides requires precise design to prevent undue flexing or rupture caused by the constant pressure cycling of a pressure swing adsorption system. The columns are fixed into place by retention mechanism 207. Various retention mechanisms are described above, and these retention mechanisms may for most cases be applied to two adsorber columns held together.

Figure 22A:
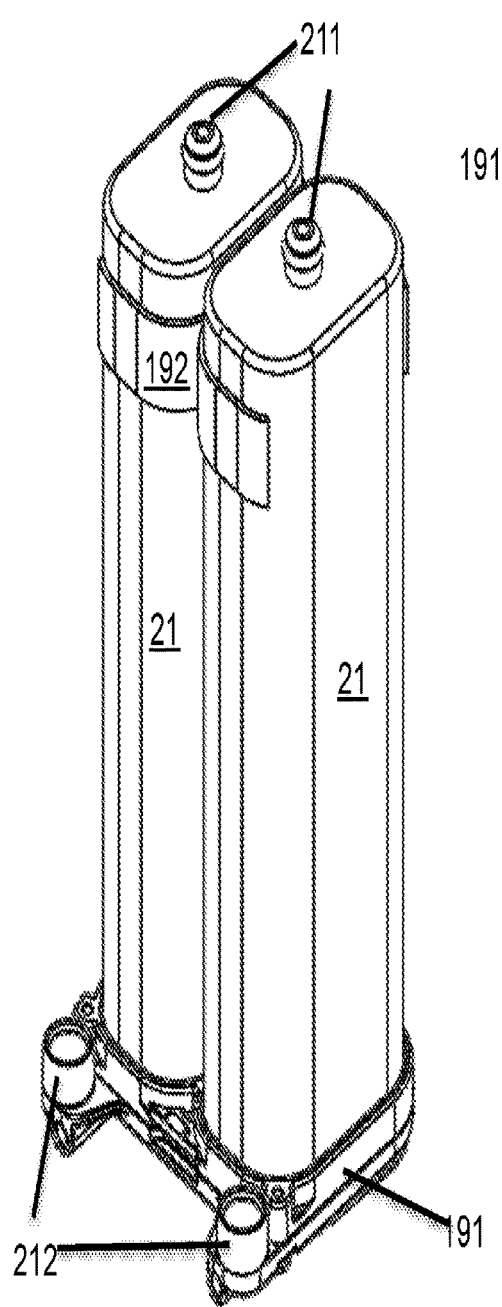
FIGS. 22A and 22B show alternative illustrative embodiments of co-attached adsorbers with common members including ports.
Figure 22B:
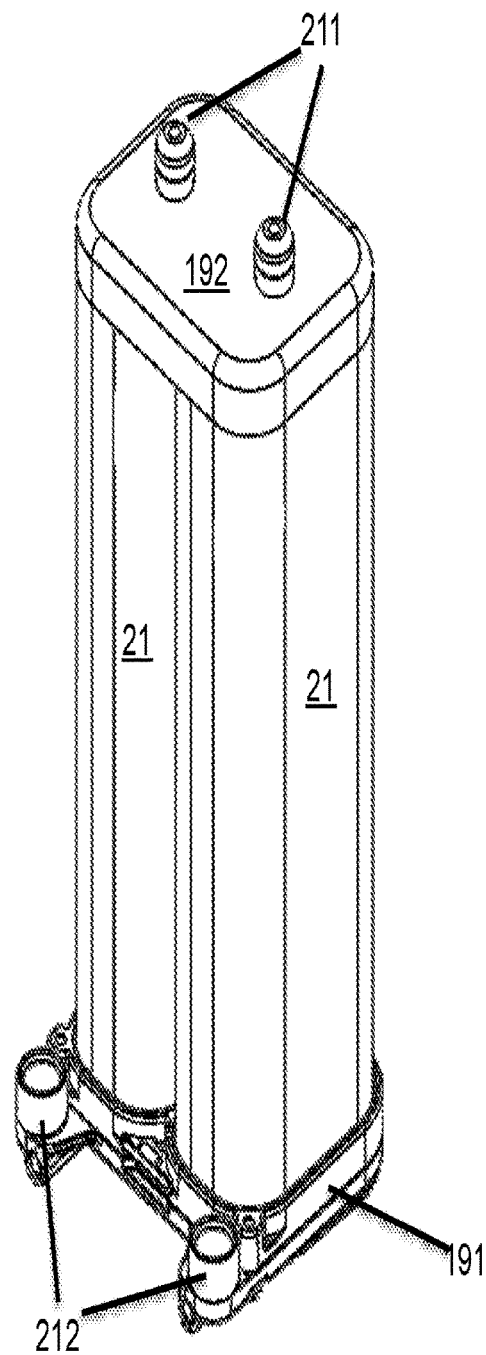

FIG. 22A shows adsorbers 21 held together with one common member 191 which includes ports 212, which both common member 191 attaches the adsorbers together and holds them with all ports 211 and 212 aligned for mounting. FIG. 22A shows the ports 211 and 212 on each end of adsorbers 21 in the configuration where the inlet and outlet flow is substantially along the same axis as the flow axis of the adsorbers. FIG. 22A additionally contains an additional common member 192 that hold the adsorbers together without integrating with the adsorber seals or ports. FIG. 22B shows an additional common member 192 at the other end of adsorbers 21, and in this embodiment, additional common member 192 includes ports 211 and additionally participates in the adsorber sealing depicted in FIGS. 24-27.

Figure 23A:
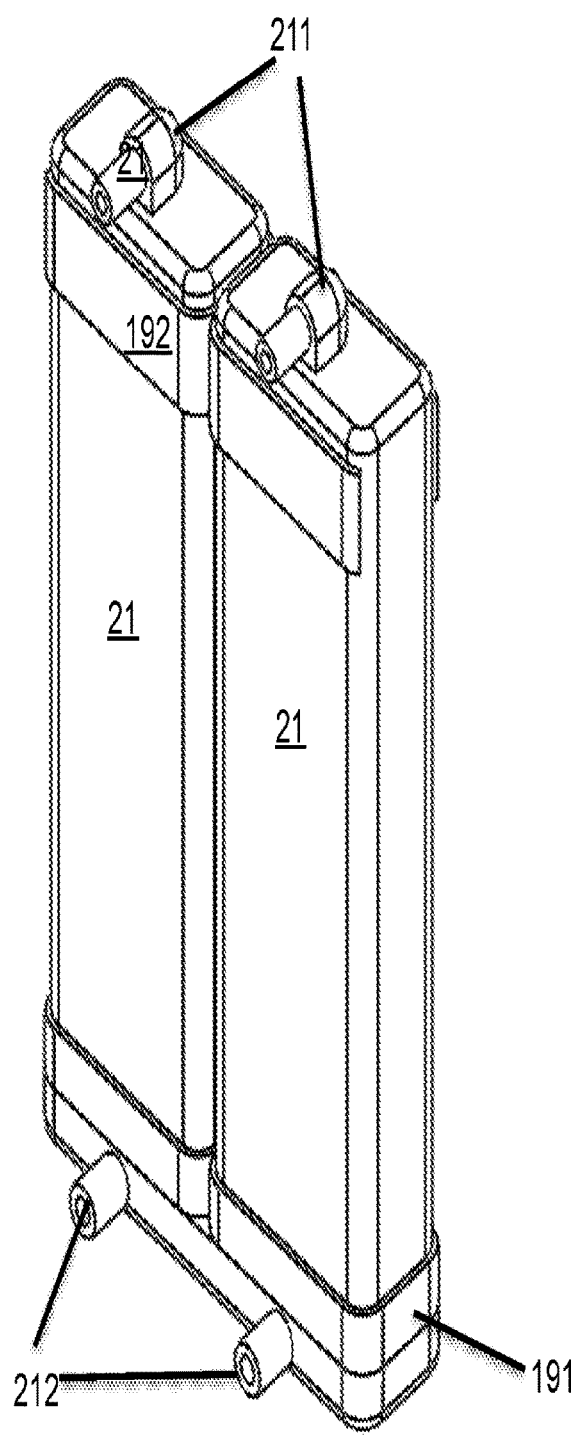
FIGS. 23A and 23B show additional illustrative embodiments of co-attached adsorbers.
Figure 23B:
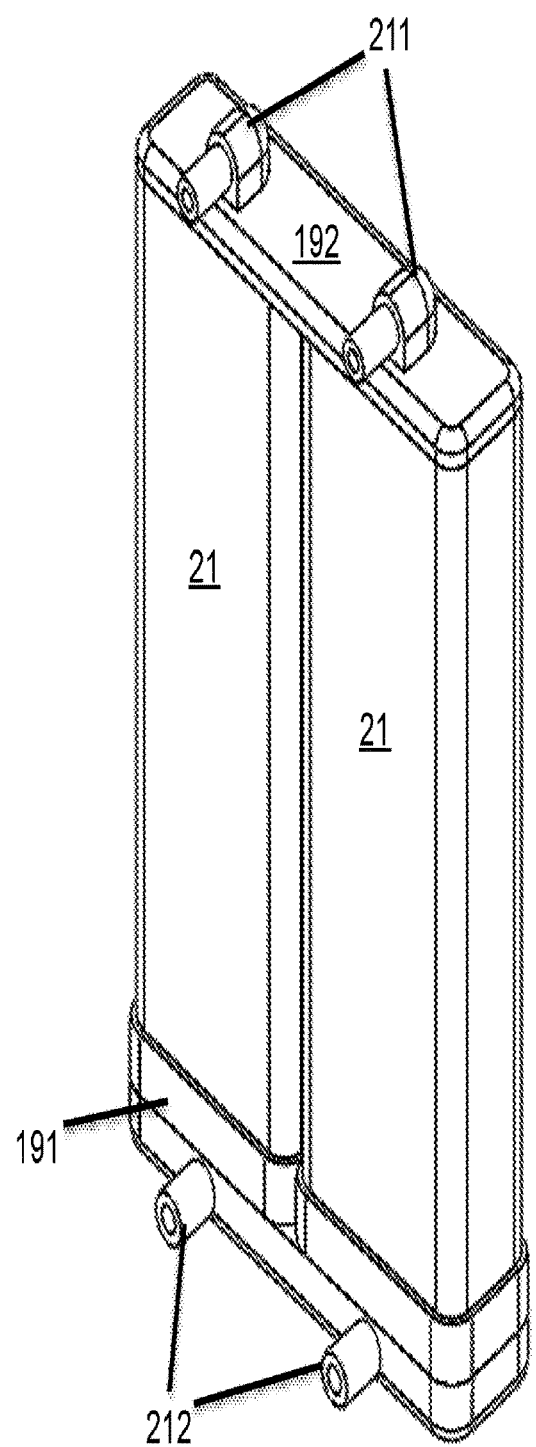

FIG. 23A shows adsorbers 21 held together with one common member 191 which includes ports 212, which both attaches the adsorbers together, seals the adsorbers as shown in FIGS. 24-27, and holds them with all ports 211 and 212 aligned for mounting. FIG. 19A shows the ports 211 and 212 on each end of adsorbers 21 in the configuration where the inlet and outlet flow is substantially perpendicular to the flow axis of the adsorbers. FIG. 23A also shows an additional common member near the other end of adsorbers 21. FIG. 23B shows an additional common member 192 at the other end of adsorbers 21, and in this embodiment, additional common member 192 includes ports 211 and adsorber seals from FIGS. 24-27. Both FIGS. 23A and 23B show the shape of the adsorbers modified to achieve a specific form factor for the completed concentrator. In the embodiment shown, the width of the adsorbers is minimized to allow for a different packing optimization compared to the embodiment in FIG. 21 or 22 or circular adsorbers of similar cross sectional area.

Figure 24:
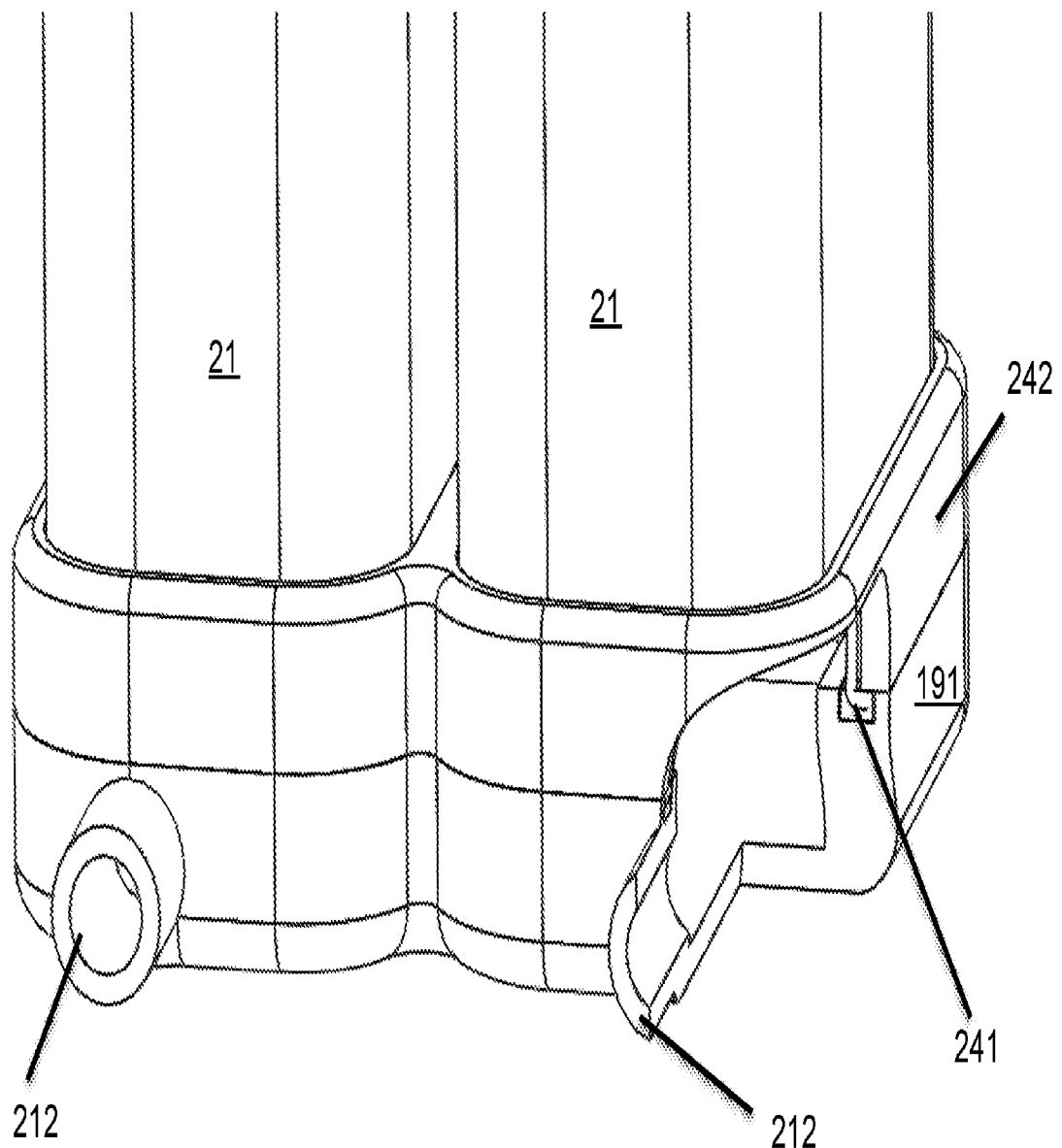
FIG. 24 shows an illustrative embodiment of face sealing and clamping adsorbers to a common member with ports.

FIG. 24 shows an illustrative embodiment for sealing adsorbers 21 to common member 191 when common member 191 includes ports 212. This and other sealing embodiments will work just as well on the other end of the adsorbers for ports 211 and for either the parallel or perpendicular port flow configurations. In the embodiment of FIG. 24 seal 241 resides between common member 191 and clamp portion 242 of the common member. Clamp 242 pushes the bottom end of adsorbers 21 onto seal 241. Clamp 242 may be pressed on or attached with fasteners. Any arrangement of clamp 242 that applies an appropriate force down on seal 241 will suffice. Seal 241 in the embodiment shown is a face seal.

Figure 25:
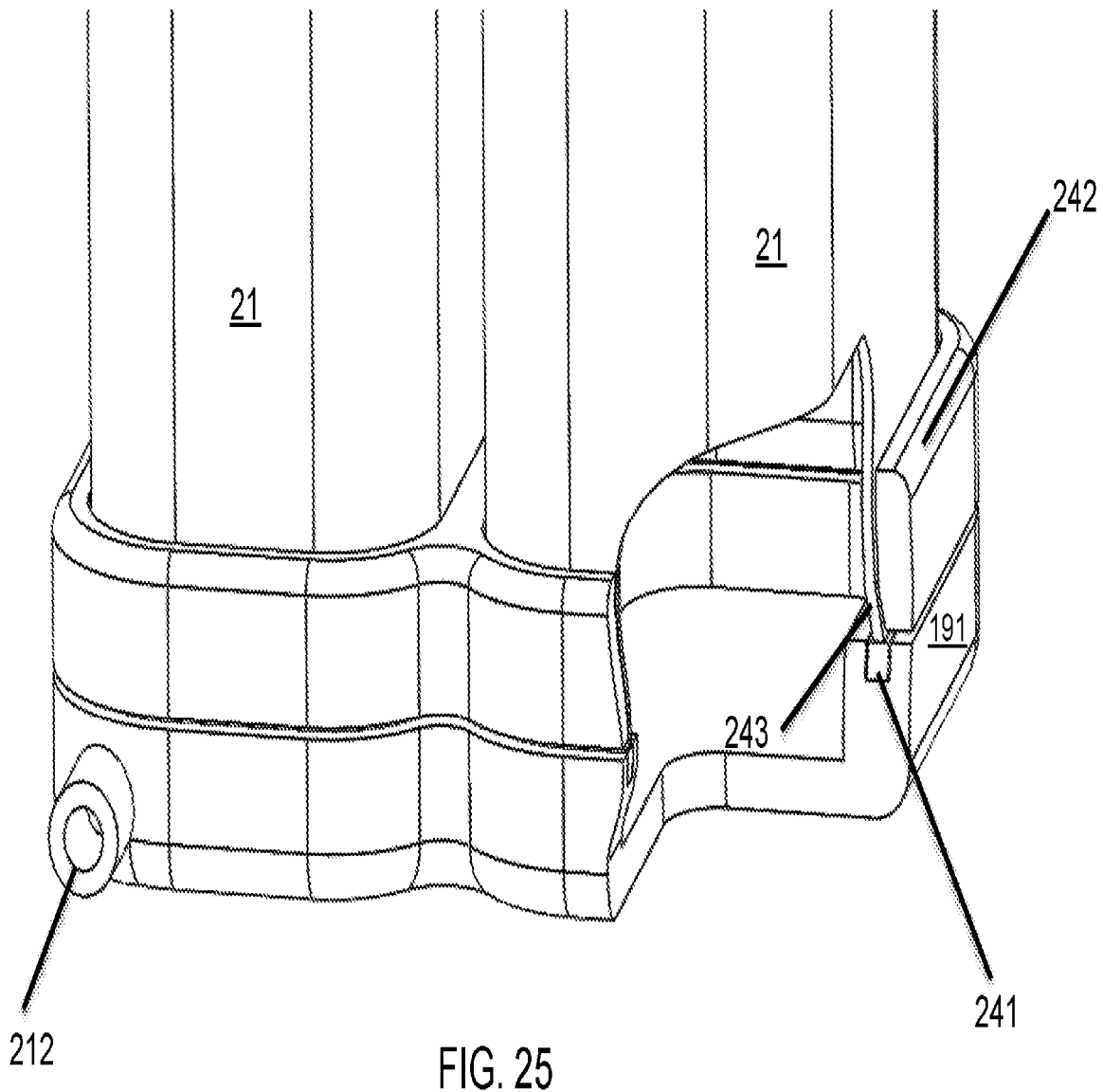
FIG. 25 shows an alternative illustrative embodiment of face sealing and clamping adsorbers to a common member with ports.

FIG. 25 shows another illustrative embodiment for sealing adsorbers 21 to common member 191 when common member 191 includes ports 212. In the embodiment of FIG. 25 seal 241 resides between common member 191 and clamp portion 242 of the common member. Both clamp portion 242 and the bottom end of the adsorbers 21 have a flared edge 243. Clamp 242 pushes the bottom end of adsorbers 21 onto seal 241. Flared edges 243 provide enhanced inward and downward force when the clamp 242 is tightened into place. Again seal 241 in the embodiment shown is a face seal.

Figure 26:
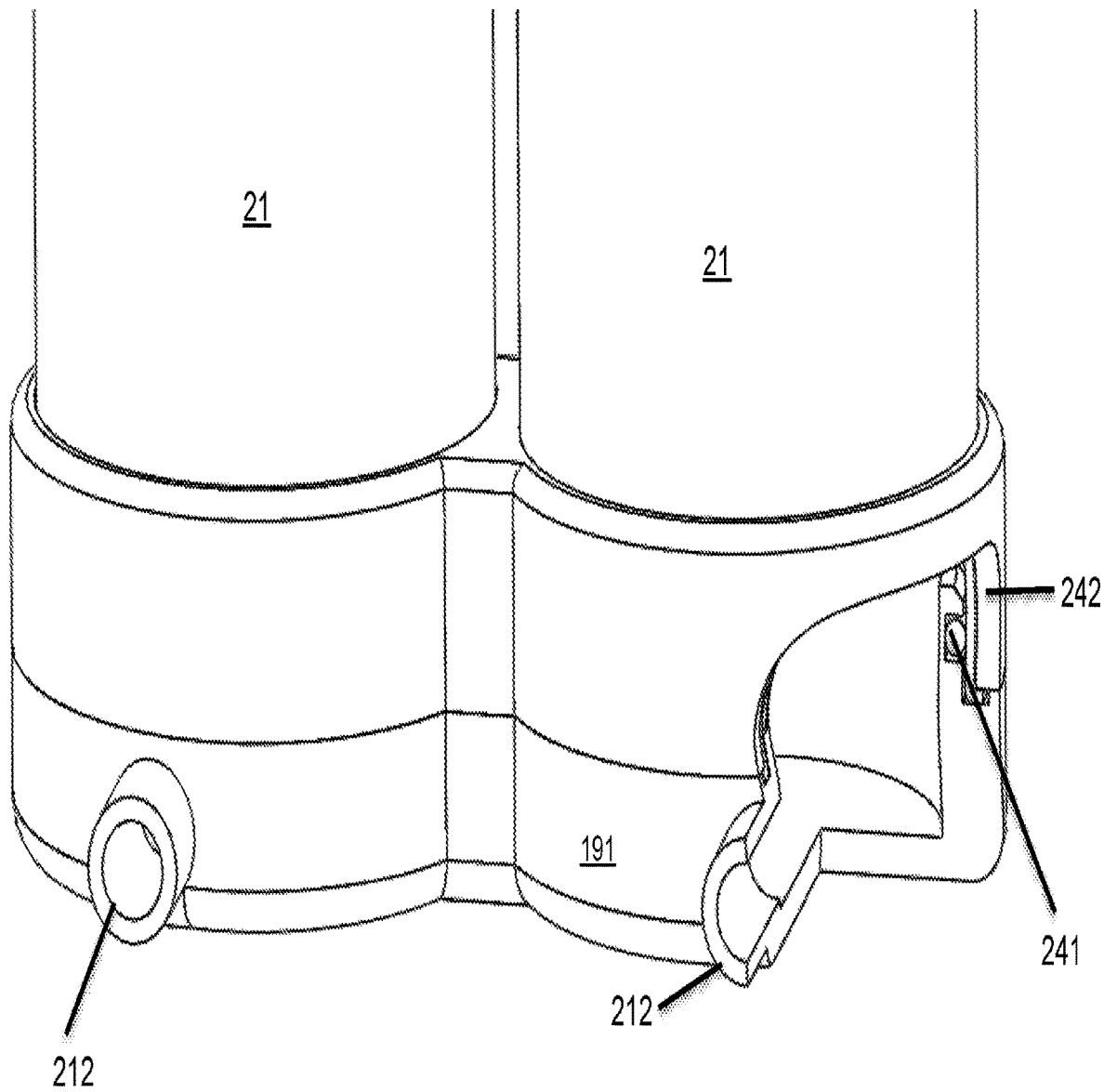
FIG. 26 shows another alternative illustrative embodiment of radial sealing and clamping adsorbers to a common member with ports.
Figure 27:
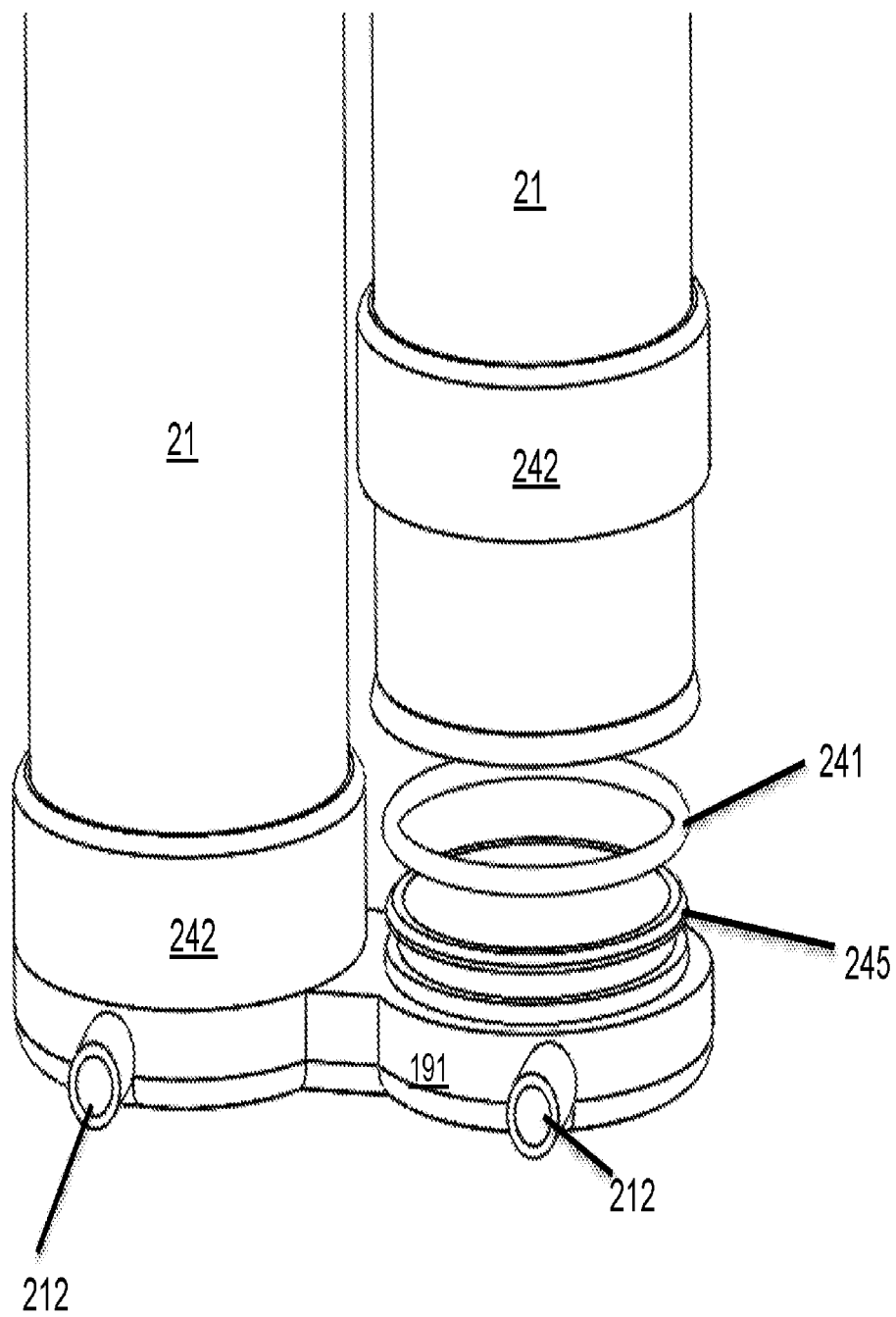
FIG. 27 shows an illustrative embodiment of radial sealing and clamping round adsorbers to a common member with ports and an additional element for forming the seal.

FIG. 26 shows another illustrative embodiment for sealing adsorbers 21 to common member 191 when common member 191 includes ports 212. In the embodiment of FIG. 26 O-ring seal 241 resides between common member 191 and the inside wall of adsorber wall 21. Clamp 242 retains common member 191 to adsorbers 21 while the o-ring seals the adsorber column FIG. 27 shows another illustrative embodiment for sealing adsorbers 21 to common member 191 when common member 191 includes ports 212. In the embodiment of FIG. 27 Each column is individually clamped and sealed to common member 191. Seal 241, an o-ring seal in the embodiment shown, resides between common member 191 and the inner wall of adsorber 21. Common member 191 includes an additional element 245 for forming the seal retaining groove for o-ring seal 241. Clamp 242 pushes the inner wall of adsorbers 21 radially against seal 241.

The foregoing description of the preferred embodiments of the present invention has shown, described and pointed out the fundamental novel features of the invention. It will be understood that various omissions, substitutions, and changes in the form of the detail of the apparatus as illustrated as well as the uses thereof, may be made by those skilled in the art, without departing from the spirit of the invention. Consequently, the scope of the invention should not be limited to the foregoing discussions, but should be defined by appended claims.

What is claimed is:

1. A portable oxygen concentrator, comprising:
    a platform, comprising:
        a housing,
        at least one compressor,
        at least one air control valve, and
        at least one adsorber receptacle comprising at least one gas connector port;
    at least two replaceable adsorbers, each of the at least two replaceable adsorbers comprising:
        a column having a top end and a bottom end, the column configured to contain a nitrogen selective adsorbent material, wherein a flow axis of gas through the column is between the top and bottom ends; and
        at least two gas connectors in fluid communication with the nitrogen selective adsorbent material and oriented parallel to the flow axis of gas through the column, wherein the at least two adsorbers are configured to mate with the platform; and
    a retention mechanism accessible on an exterior of the platform;
    wherein the retention mechanism removably secures the at least two adsorbers to the platform;
    wherein the retention mechanism is at least one of tool or hand operable.

2. The portable oxygen concentrator of claim 1, wherein the retention mechanism comprises a rotatable tab.

3. The portable oxygen concentrator of claim 2, wherein the rotatable tab is rotatable into a slot to removably secure the at least two adsorbers to the platform.

4. The portable oxygen concentrator of claim 2, wherein the retention mechanism comprises a screw or knob coupled to the rotatable tab.

5. The portable oxygen concentrator of claim 1, wherein the retention mechanism comprises a sliding spring loaded plunger and a receptacle which mates with the spring loaded plunger, and wherein the spring loaded plunger snaps into the receptacle when the at least two adsorbers are mated to the at least one adsorber receptacle thereby retaining the at least two adsorbers and actuation of the spring loaded plunger releases the at least two adsorbers.

6. The portable oxygen concentrator of claim 5, where the portable oxygen concentrator weighs less than 8 pounds.

7. The portable oxygen concentrator of claim 1, wherein the at least two adsorbers are joined by at least one common member.

8. The portable oxygen concentrator of claim 7, wherein the at least one common member is disposed at one end of the at least two adsorbers.

9. The portable oxygen concentrator of claim 7, wherein the at least one common member forms a portion of an adsorber seal.

10. The portable oxygen concentrator of claim 7, wherein the portable oxygen concentrator weighs less than 4 pounds.

11. The portable oxygen concentrator of claim 1, wherein the portable oxygen concentrator weighs less than 10 pounds.

12. The portable oxygen concentrator of claim 1, further comprising a rechargeable battery capable of running the portable oxygen concentrator for greater than 2 hours.

13. The portable oxygen concentrator of claim 12, further comprising a case configured to enclose the platform, the at least two adsorbers, and the battery when the platform, the at least two adsorbers, and the battery are mated together.

14. The portable oxygen concentrator of claim 1, wherein a leak rate of the at least one gas connector port is less than about 10 Standard Cubic Centimeters per Minute at a maximum rated operating pressure of the column.

15. The portable oxygen concentrator of claim 1, wherein the portable oxygen concentrator produces less than 45 decibels acoustic noise while operating.

16. The portable oxygen concentrator of claim 1, wherein a total volume of the portable oxygen concentrator is less than 600 cubic inches.

17. The portable oxygen concentrator of claim 1, wherein the at least two gas connectors each comprise an inlet port and an outlet port for each of the at least two adsorbers, wherein the inlet ports and the outlet ports each contain at least one radial seal.

18. The portable oxygen concentrator of claim 1, further comprising at least one air filter.

19. The portable oxygen concentrator of claim 1, wherein each of the at least two adsorbers is round in shape.

20. The portable oxygen concentrator of claim 1, wherein the portable oxygen concentrator is configured to provide a product gas stream comprising an oxygen concentration between 80% and 95% purity.

* * * * *